(12) United States Patent
Venkatraman et al.

(10) Patent No.: US 10,272,040 B2
(45) Date of Patent: Apr. 30, 2019

(54) LIPOSOMAL FORMULATION FOR OCULAR DRUG DELIVERY

(75) Inventors: Subramanian Venkatraman, Singapore (SG); Jayaganesh V. Natarajan, Singapore (SG); Tina Wong, Singapore (SG); Yin Chiang Freddy Boey, Singapore (SG)

(73) Assignees: Nanyang Technological University, Singapore (SG); Singapore Health Services Pte Ltd, Singapore (SG)

( * ) Notice: Subject to any disclaimer, the term of this patent is extended or adjusted under 35 U.S.C. 154(b) by 639 days.

(21) Appl. No.: 13/816,640

(22) PCT Filed: Aug. 12, 2011

(86) PCT No.: PCT/SG2011/000281
§ 371 (c)(1),
(2), (4) Date: Apr. 30, 2013

(87) PCT Pub. No.: WO2012/021107
PCT Pub. Date: Feb. 16, 2012

(65) Prior Publication Data
US 2013/0216606 A1  Aug. 22, 2013

Related U.S. Application Data

(60) Provisional application No. 61/372,962, filed on Aug. 12, 2010.

(51) Int. Cl.
*A61K 9/127* (2006.01)
*A61K 31/5575* (2006.01)
(Continued)

(52) U.S. Cl.
CPC ............ *A61K 9/127* (2013.01); *A61K 9/0048* (2013.01); *A61K 31/215* (2013.01); *A61K 31/5575* (2013.01)

(58) Field of Classification Search
CPC .............................. A61K 9/127; A61K 9/1271
(Continued)

(56) References Cited

U.S. PATENT DOCUMENTS 4,599,353 A  7/1986  Bito
4,681,582 A * 7/1987  Yamamoto .......... A61M 31/002
                                                    424/450
(Continued)

FOREIGN PATENT DOCUMENTS

EP          0 093 380    * 11/1983
WO   WO-1989003384 A1    4/1989
(Continued)

OTHER PUBLICATIONS

Camras, C.B., et al in Ophthalmology, vol. 103, # 11, 1996, pp. 1916-1924.*
(Continued)

*Primary Examiner* — Gollamudi Kishore
(74) *Attorney, Agent, or Firm* — Cesari and McKenna, LLP

(57) ABSTRACT

The present invention is directed to a liposomal formulation for ocular drug delivery comprising (i) liposomes comprising at least one lipid bilayer, and (ii) a prostaglandin drug and/or a prostaglandin derivative associated in the liposomes, wherein the liposomes have a mean diameter of less than 2μm. The present invention is also directed to a pharmaceutical comprising the liposomal formulation and a method of producing the liposomal formulation for ocular drug delivery. Additionally, the present invention is directed to a method of treating or preventing an ocular disease, comprising administering the liposomal formulation or the pharmaceutical composition to a subject in need thereof.

26 Claims, 14 Drawing Sheets

(51) Int. Cl.
*A61K 31/215* (2006.01)
*A61K 9/00* (2006.01)

(58) Field of Classification Search
USPC ........................................................ 424/450
See application file for complete search history.

(56) References Cited

U.S. PATENT DOCUMENTS

| | | | |
|---|---|---|---|
| 4,938,965 A * | 7/1990 | Shek | A61K 9/0048 424/450 |
| 4,963,297 A * | 10/1990 | Madden | A61K 9/1277 264/4.1 |
| 5,082,664 A * | 1/1992 | Lenk | A61K 9/127 264/4.3 |
| 5,120,870 A | 6/1992 | Mizushima et al. | |
| 5,316,771 A * | 5/1994 | Barenholz | A61K 9/1278 264/4.1 |
| 5,478,819 A * | 12/1995 | Tarpila | A61K 9/127 424/450 |
| 5,662,931 A * | 9/1997 | Munechika | A61K 9/1277 264/4.1 |
| 5,846,561 A * | 12/1998 | Margalit | A61K 9/1271 264/4.3 |
| 5,925,375 A * | 7/1999 | Lenk | A61K 9/127 424/450 |
| 6,225,348 B1 | 5/2001 | Paulsen | |
| 6,486,208 B1 | 11/2002 | Castillo et al. | |
| 6,623,671 B2 * | 9/2003 | Coe | A61K 9/1277 264/4.3 |
| 7,332,526 B2 | 2/2008 | Bakhit et al. | |
| 7,560,100 B2 | 7/2009 | Pinchasi et al. | |
| 7,592,325 B2 | 9/2009 | Jimenez et al. | |
| 8,293,789 B2 | 10/2012 | Jimenez-Bayardo et al. | |
| 8,409,606 B2 | 4/2013 | Sawhney et al. | |
| 8,470,784 B2 | 6/2013 | Liu et al. | |
| 8,771,745 B2 | 7/2014 | Robinson et al. | |
| 2001/0006648 A1 | 7/2001 | Yamauchi et al. | |
| 2003/0068365 A1 | 4/2003 | Suvanprakorn et al. | |
| 2003/0212001 A1 | 11/2003 | Peri et al. | |
| 2004/0137068 A1 | 7/2004 | Bhushan | |
| 2004/0224010 A1 * | 11/2004 | Hofland | A61K 9/127 424/450 |
| 2004/0224011 A1 * | 11/2004 | Rodrigueza | A61K 9/0019 424/450 |
| 2005/0054723 A1 * | 3/2005 | Stjernschantz | A61K 9/0048 514/530 |
| 2005/0220768 A1 | 10/2005 | McVey et al. | |
| 2005/0228048 A1 | 10/2005 | Asada et al. | |
| 2006/0165744 A1 | 7/2006 | Jamil et al. | |
| 2006/0188481 A1 | 8/2006 | Mori | |
| 2006/0211770 A1 | 9/2006 | Chang et al. | |
| 2006/0246145 A1 | 11/2006 | Chang et al. | |
| 2007/0026061 A1 | 2/2007 | Ali et al. | |
| 2007/0224255 A1 | 9/2007 | Moscoso Del Prado et al. | |
| 2007/0292496 A1 * | 12/2007 | Herrero Vanrell | A61K 9/0048 424/450 |
| 2008/0021101 A1 | 1/2008 | Jimenez-Bayardo et al. | |
| 2008/0227099 A1 * | 9/2008 | Lawn | C07K 14/705 435/6.18 |
| 2008/0268020 A1 | 10/2008 | Philips et al. | |
| 2009/0234005 A1 | 9/2009 | Ishida et al. | |
| 2009/0280158 A1 | 11/2009 | Butuner | |
| 2009/0318549 A1 | 12/2009 | Butuner | |
| 2010/0112016 A1 | 5/2010 | Carli et al. | |
| 2010/0209477 A1 | 8/2010 | Butuner et al. | |
| 2010/0247606 A1 | 9/2010 | Robinson et al. | |
| 2010/0291226 A1 | 11/2010 | Mazzone et al. | |
| 2011/0008421 A1 | 1/2011 | Hara et al. | |
| 2011/0028477 A1 | 2/2011 | Aleo et al. | |
| 2011/0052493 A1 | 3/2011 | Fumero et al. | |
| 2011/0152264 A1 | 6/2011 | Reunamaki et al. | |
| 2011/0294730 A1 | 12/2011 | Shantha et al. | |
| 2012/0184552 A1 | 7/2012 | Nakajima et al. | |
| 2012/0264681 A1 | 10/2012 | Bralman-Wiksman et al. | |
| 2012/0321719 A1 | 12/2012 | McDonnell et al. | |
| 2013/0053794 A1 | 2/2013 | Cadden et al. | |
| 2013/0216606 A1 | 8/2013 | Venkatraman et al. | |
| 2013/0273065 A1 | 10/2013 | Dana et al. | |
| 2013/0281454 A1 | 10/2013 | Schiffman et al. | |
| 2013/0309330 A1 | 11/2013 | Mastronardi | |
| 2014/0025022 A1 | 1/2014 | Cadden et al. | |
| 2014/0121612 A1 | 5/2014 | Rubin et al. | |
| 2014/0193347 A1 | 7/2014 | Thuresson et al. | |
| 2014/0213646 A1 | 7/2014 | Wong et al. | |

FOREIGN PATENT DOCUMENTS

| | | |
|---|---|---|
| WO | WO-1998043616 A1 | 10/1998 |
| WO | WO-2009051670 A3 | 4/2009 |
| WO | WO-2011053792 A2 | 5/2011 |
| WO | WO-2011/098578 A2 | 8/2011 |
| WO | WO-2012021107 A2 | 2/2012 |
| WO | WO-2013164671 A1 | 11/2013 |
| WO | WO-2014039012 A1 | 3/2014 |
| WO | WO-2014153733 A1 | 10/2014 |

OTHER PUBLICATIONS

Bito, L.Z. et al in Journal of Lipid Regulators, vol. 6, 1993, pp. 535-543.*
International Search Report for Application No. PCT/SG2011/000281, dated Oct. 12, 2011.
International Search Report for Application No. PCT/SG2011/000281, dated Dec. 5, 2012.
Al-Muhammad, J. et al., *Studies on the Formulation and In Vitro Release of Ophthalmic Liposomes Containing Dexamethasone Sodium Phosphate*, J Microencapsul, 13(2) (1996) pp. 123-130.
Almog, R., et al., *Stability of Sonicated Aqueous Suspensions of Phospholipids Under Air*, Chem Phys Lipids 60 (1991) pp. 93-99.
Amano, S., et al., *A Case of Keratoconus Progression Associated with the Use of Topical Latanoprost*, Jpn J Ophthalmol 52 (2008) pp. 334-336.
Bartlett, G., *Phosphorus Assay in Column Chromatography*, J Biol Chem 234 (1959) pp. 466-468.
Bhardwaj, U., et al., *Physiochemical Properties of Extruded and Non-Extruded Liposomal Containing the Hydrophobic Drug Dexamethasone*, Int J Pharm; 388 (1-2) (2010) pp. 181-189.
Bolean, M., et al., *The Effect of Cholesterol on the Reconstitution of Alkaline Phosphatase into Liposomes*, Biophys Chem 152 (2010) pp. 74-79.
Costas, D., *Differential Scanning Calorimetry (DSC): A Tool to Study the Therman Behavior of Lipid Bilayers and Liposomal Stability*, J Liposome Res 18 (2008) pp. 159-173.
Detoni, C., et al., *Essential Oil from Zanthoxylum Tingoassuiba Loaded into Multilamellar Liposomes Useful as Antimicrobial Agents*, J Microencapsul 26 (2009) pp. 684-691.
Ebrahim, S., et al., *Applications of Liposomes in Ophthalmology*, Surv Ophthalmol 50 (2005) pp. 167-182.
Hailing, K, et al., *Membrane Properties of Plant Sterols in Phospholipid Bilayers as Determind by Differential Scanning Calorimetry, Reasonance Energy Transfer and Detergent-Induced Solubilization*, Biochin Biopys Acta 1664 (2004) pp. 161-171.
Hathout, R., et al., *Liposomes as an Ocular Delivery Ststem for Acetazolamide: In Vitro and In Vivo Studies*, AAPS Pharm Scie Tech 8 (2007) pp. 1-12.
Himle, E., et al., *Distribution of Liposome Incorporated Carboxyfluorescein in Rabbit Eyes*, J Microencapsul 8(1991) 391-399.
Hironaka, K., et al., *Design and Evaluation of a Liposomal Delivery Ststem Targeting the Posterior Segment of the Eye*, J Control Release 136 (2009) pp. 247-253.
Huq, F., *Molecular Modeling Analysis of the Metabolism of Latanoprost*, J Rhatmooologxond, Toxicology 2 (2007) pp. 359-365.
Jarvinen, K., et al., *Ocular Absorption Following Topical Delivery*, Adv Drug Dev Rev, 16 (1995) pp. 3-19.
Kaur, I., et al., *Ocular Preparations: The Formulation Approach*, Drug Dev Ind Pharm 28 (2002) pp. 473-493.

(56) References Cited

OTHER PUBLICATIONS

Lang, J.C., *Ocular Drug Delivery Conventional Ocular Formulations*, Adv Drug Deliv Rev 16 (1995) pp. 39-43.
Lee, V., *Mechanisms and Facilitation of Corneal Drug Penetration*, J Control Release 11 (1990) pp. 79-90.
Lee, V., et al., *Ocular Drug Bioavailability from Topically Applied Liposomes*, Surv. Opthamol 2 (1985) pp. 3-19.
Lee, V., et al., *Precorneal Factors Influencing the Ocular Distribution of Topically Applied Liposomal Insulin*, Curr Eye Res 2 (1984) pp. 585-591.
Lewis, T., et al., *Optometric Clinical Practice Guidelines Care of the Patient with Open Angle Glaucoma*, Reference Guide for Clinicals, American Optometric Associates $2^{nd}$ Edition. (2002).
Lin, H., et al., *The Preparation of Norfloxacin-Loaded Liposomes and their In-Vitro Evaluation in Pig's Eye*, J Pharm Pharmacol 48 (1996) pp. 801-805.
Liu, J., et al., *Liposome Formulation of a Novel Hydrophobic Aryl-Imidazole Compound for Anti-Cancer Therapy*, Cancer Chemother Pharmacol 58 (2006) pp. 306-318.
Linden, C., et al., *Effects of IOP Restoration and Blodd-aqueous Barrier After Long-Term Treatment with Latanoprost in Open Angle Glaucoma and Hypertension*, Br J Ophtalmol 81 (1997) pp. 370-372.
Mannock, D., et al., *A Colorimetric and Spectroscopic Comparison of the Effects of Ergosterol and Cholesterol on the Thermotrpic Phase Behavior and Organization of Dipalmitoylphosphatidylcholine Bilayer Membranes*, Biochim Biophys Acta 1798 (2010) pp. 376-388.
Mehnert, W., et al., *Solid Lipid Nanoparticles: Production, Characterization and Applications*, Adv Drug Deliv Rev 47 (2001) pp. 165-196.
Meisner, D., et al., *Liposome Ocular Delivery Systems*, Adv Drug Deliv Rev; 16 (1981) pp. 75-93.
Meisner, D., et al., *Liposome Ocular Delivery Systems*, Adv Drug Deliv Rev; 16 (1995) pp. 75-93.
Mohammed, et al., *Liposome Formulation of Poorly Water Soluble Drugs: Optimization of Drug Loading and ESEM Analysis of Stability*, Int J. Pharm 285, pp. 23-34.
Nagle, J, et al., *Structure of Lipid Bilayers*, Biochim Biophys Acta 1469 (2000) pp. 159-195.
Netland P., et al., *Travoprost Compared with Latanoprost and Timolol in Patients with Open-Angle Glaucoma or Ocular Hypertension*, Am J Ophthalmol 132 (2001) pp. 472-484.

Niesmann, M., *The Use of Liposomes as Drug Carriers in Ophthalmology*, Crit Rev Ther Drug Carrier Syst 9 (1992) pp. 1-38.
Nordmann, J., et al., *Vision Related Quality of Life and Topical Glaucoma Treatment Side Effects*, Health Qual Life Outcomes 1 (2003).
Perez-Soler, R., et al., *Lipophilic Cisplatin Analogues Entrapped in Liposomes: Role of Intraliposomal Drug Activation in Biological Activity*, Cancer Res, 52 (1992) pp. 6341-6347.
Quigley, H., *Number of People with Glaucoma Worldwide*, Br J Opthalmol 80 (1996) pp. 389-393.
Roianaskul, Y., et al.,*The Cytoskeleton of the Cornea and its Role in Tight Junction Permeability*, Int J Pharm 68 (1991) pp. 135-149.
Roianasakul, Y., et al., *Transport Mechanisms of the Cornea: Characterization of Barrier Permselectivity*, Int J Phat 55 (1989) pp. 237-246.
Russo, A., et al.,*Latanoprost Ophthalmic Solution in the Treatment of Open Angle Glaucoma or Raised Intraocular Pressure: A Review*, Clin Ophthalmol 2 (2008) pp. 897-905.
Schaeffer, H., et al., *Liposomes in Topical Drug Delivery*, Invest Ophthalmol Vis Sci 22 (1982) pp. 220-227.
Shah, M., et al., *Neutralising Antibody to TGF-beta 1,2 Reduces Cutaneous Scarring in Adult Rodents*, J Cell Sci 107 (1994) pp. 1137-1157.
Sila-on. W., et al., *Influence of Incorporations Methods on Partitioning Behavior of Lipophilic Drugs into Various Phases of a Parenteral Lipid Emulsion*, AAPS Pharma Sci Tech 9 (2008) pp. 684-692.
Smolin, G., et al., *Idoxuridine-Liposome Therapy for Herpes Simplex Keratitis*, Am J Ophthalmol 91 (1981) pp. 220-225.
Sou, K., et al., *Bone Marrow-Targeted Liposomal Carriers: A Feasibility Study in Nonhuman Primates*, Nanomedicine, 5(1) (2010) pp. 41-49.
Stratford, R., Jr., et al., *Ocular Distribution of Liposome Encapsulated Epinephrine and Inulin in the Albino Rabbit*, Curr Eye Res 2 (1983) pp. 377-386.
Wells, A., et al., *A Pilot Study of a System for Grading of Drainage Blegs After Glaucoma Surgery*, J Glaucoma 13 (2004) pp. 454-460.
Yasukawa, T., et al., *Drug Delivery Systems for Vitreoretinal Disease*, Prog Retin Eye Res 23 (2004) pp. 253-281.
Yusuke, S., et al., *Stability of Latanoprost in an Opthalmic Lipid Emulsion Using Polyvinyl Alcohol*, Int J Pharm, 305 (2005) pp. 176-179.

\* cited by examiner

LIPOSOMAL FORMULATION FOR OCULAR DRUG DELIVERY

CROSS REFERENCE TO RELATED APPLICATIONS

This application is a National Stage Entry of PCT/SG2011/000281, filed Aug. 12, 2011, which claims the benefit of U.S. Provisional Application No. 61/372,962, filed Aug. 12, 2010. The contents of said applications are incorporated herein by reference for all purposes, including an incorporation of any element or part of the description, claims or drawings not contained herein and referred to in Rule 20.5(a) of the PCT, pursuant to Rule 4.18 of the PCT.

TECHNICAL FIELD

Various embodiments relate to the field of liposomal formulations for drug delivery, in particular liposomal formulations for ocular drug delivery.

BACKGROUND

The pressure within the eyeball is naturally maintained by a continuous flow of aqueous humour produced by ciliary body. It drains out the excess eyeball fluid through channels called the trabecular meshwork. If the outflow is blocked, the aqueous humour builds up inside the eye, increasing the pressure within the eyeball. This pressure needs to be reduced, as otherwise it can damage the optic nerve, resulting in an optic neuropathy and irreversibly impair vision as a result. This condition is known as glaucoma—a disease that affects more than 60 million worldwide and is the second leading cause of blindness. Intraocular pressure (IOP) remains the key modifiable risk factor in glaucoma.

Latanoprost is a prostaglandin analogue and is a potent drug that can reduce the IOP of the eye by increasing aqueous outflow through the uveoscleral pathway. The ester bond of latanoprost gets easily hydrolyzed forming IPA (isopropyl alcohol) and latanoprost acid, which is more hydrophilic and experiences a higher penetration resistance through the epithelium and endothelium of the cornea. Thus, this causes stability problems for this drug in aqueous, low and high pH range. To avoid this instability, coupled with the low solubility, it is mainly delivered in the form of, for example, oil/water emulsion, and lipid/buffer emulsion (for example, Xalatan). There is another unavoidable issue of irreversible yellow pigmentation of corneal epithelium after regular application of commercial eye drop for longer period (for example, beyond three months). This pigmentation is attributed to the presence of benzalkonium chloride, which acts as a preservative for latanoprost in the commercial eye drop.

In addition to the stability problem of the drug, there exist several challenges in ocular drug delivery, e.g. (i) heavy tear drainage cum dilution mechanism washes away any substance from corneal/conjunctival epithelium cell; (ii) the trilaminate corneal epithelium has a stromal cell layer sandwiched between highly lipophilic outer layer and hydrophilic inner layer and each of these layers contributes to resistance of various amount depending on the lipophilicity of drug. Further, of the two common pathways (paracellular and transcellular) for the transport of drug molecules, the drug molecules would predominantly use the transcellular path to cross the cornea, where the lipophilicity and dissociation constant (pKa) are the major parameters that decide the entry of drug molecules.

Because of all these factors, a mere 5% of the free drug applied on the corneal epithelium successfully penetrates through the cornea. Thus, the effective drug concentration reaching the aqueous humor often falls below the therapeutic limit and repeated administration is necessary because a substantial portion goes into the conjunctival sac and enters the circulation, causing undesirable side effects. In order to improve bioavailability of drug, the transport barrier as well as prolonging the retention of the drug carrier in the anterior segment of the eye would be necessary.

Specifically, for the drug latanoprost, which is currently administered by daily eye drops, patient compliance and adherence to the strict regimen is a serious matter. Daily application, poor ocular bioavailability of topical application of drugs, and other long-term side effects affect patient compliance, which leads to disease progression.

Sustained topical delivery in the front of the eye is made difficult because of drainage. Therefore, formulations like eye drops, ointments although easy to apply get cleared away with only a proportion of the drug getting transported through these barriers. Therefore, to avoid (i) frequent administration and (ii) undesirable toxic effects of drug, liposomal formations might be a possible and more favoured alternative delivery system. The liposome is a lipid vesicle that possesses a hydrophilic core and hydrophobic boundary wall along with potential for specificity by surface modification. This helps liposomes to become effective for delivering a wide range of drugs and prevents the drug from being degraded by external physiological conditions. Delivery of ocular drugs using liposomal formulation relates to various problems associated with drug penetration, stability, efficacy, and sustainability. However, delivery of a hydrophobic drug due to its low water solubility limit is considerably more challenging. The limited bilayer space availability in the lipid bilayer often limits the loading of a lipophilic drug and is the most significant hurdle in developing liposomes for sustained delivery of hydrophobic entities, including latanoprost.

A transparent drug loaded liposomal formulation that can evade mononuclear phagocytic uptake may provide as a good alternative. Liposomes, which have been shown to be biocompatible nanocarriers for ocular use, allows for delivery of both the lipophilic drug molecule as well as its hydrophilic active products, due to its physical structure of a polar core and lipophilic bilayer. Liposomal encapsulation protects drug molecules from enzymatic hydrolysis in the physiological environment while in circulation, and thus increases stability.

However, the size of small uni-lamellar vesicle (SUV, 20-50 nm) or large uni-lamellar vesicle (LUV, ~100 nm) often restricts its transport through epithelial layers, and also permits rapid clearance during topical administration. Thus, several modifications of liposomes have been reported: (i) surface modification with charged lipids which can make vesicles adhere to the oppositely (negatively) charged corneal epithelium, (ii) increasing the lipophilicity of the drug molecules, and (iii) modifying the integrity of corneal epithelium transiently by using a penetration enhancer. Such modifications would facilitate the first stage of the entry of drug molecules, while the subsequent permeation would be governed by pKa, hydrophilicity/lipophilicity of the drug molecules.

Various routes of administration of liposomal formulations comprise topical administration, intravitreal, subconjunctival and systemic injection.

Previous studies on topical application of liposomes demonstrated poor penetration into the eye; while studies on subconjunctival injections on other IOP-lowering drugs show limited sustainability.

For example, in in vivo studies for topically applied liposome loaded drug formulations, positively charged egg phosphatidyl choline (PC): cholesterol (CH): stearyl amine (7:4:1) multilamellar vesicles (MLVs) loaded with acetazolamide, when applied topically, shows the highest lowering of IOP (−7.8 mmHg) after 3 hours. However this lowering lasts only for about 8 hours.

Comparing sub-conjunctival delivery of 6-carboxyfluorescein (as a "model" drug) in rabbit eyes in aqueous solution and liposomal formulation, the released drug concentration is noticeably high after 30 mins and transitory conjunctivitis (i.e., common swelling due to excess drug concentration) is observed, but no side effect has been reported. The liposomal formulation shows detectable levels of carboxyfluorescein at the injection site of sub-conjunctiva along with sclera, cornea, choroid and retina after 7 days of injection, but the reason attributing to the sustainability/retention in this study has not clearly been understood. Furthermore, it is also not clearly understood whether drug-loaded liposomes vesicles in the sub-conjunctiva behave like a depot system or actually undergo circulation and endocytosis.

In vitro application of norfloxacin loaded liposome onto cornea has improved drug retention when compared to free drug solution. They indicate a probable corneal endocytic uptake of norfloxacin loaded liposome through the corneal membrane. There appears to be no other report of enhanced drug retention in the anterior segment of the eye. The pharmacokinetics of drug release from the liposome vesicle and penetration through corneal epithelium is still poorly understood. If the drug release from these vehicles is appreciably slow, then clearance will dominate drug adsorption and diffusion through corneal epithelium. Therefore, released drug will be too diluted (tear dilution) to have an adequate gradient to cross the corneal epithelium. Thus, it may perform poorer than even free drug.

Although liposomal carriers have been evaluated for delivery of drugs topically on the front of the eye, none have been successful to date for sustained release. Very few studies have been reported on the fate of liposomes injected subconjunctivally. Nevertheless, subconjunctival injection may be an attractive option for sustained delivery of anti-glaucoma agents, provided the effects can be sustained for at least 1 month, or preferably longer. Specifically, for the delivery of latanoprost (a prostaglandin derivative that is currently administered via once-a-day eye drops), there is no report on comparison of in vitro and in vivo release behavior.

Thus it is an object of the present invention to provide a liposomal formulation for ocular drug delivery that improves the sustained release of the drug and circumvents the problems presented by the strict regime of patient compliance and adherence.

SUMMARY

In a first aspect, the present invention relates to liposomal formulation for ocular drug delivery comprising (i) liposomes comprising at least one lipid bilayer, and (ii) a prostaglandin drug and/or a prostaglandin derivative associated in the liposomes, wherein the liposomes have a mean diameter of less than 2 μm.

According to a second aspect, the present invention relates to a pharmaceutical composition comprising the liposomal formulation.

According to a third aspect, the present invention relates to a method of producing the liposomal formulation for ocular drug delivery.

According to a fourth aspect, the present invention relates to a method of treating or preventing an ocular disease, comprising administering the liposomal formulation or the pharmaceutical composition to a subject in need thereof.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Figure 1:
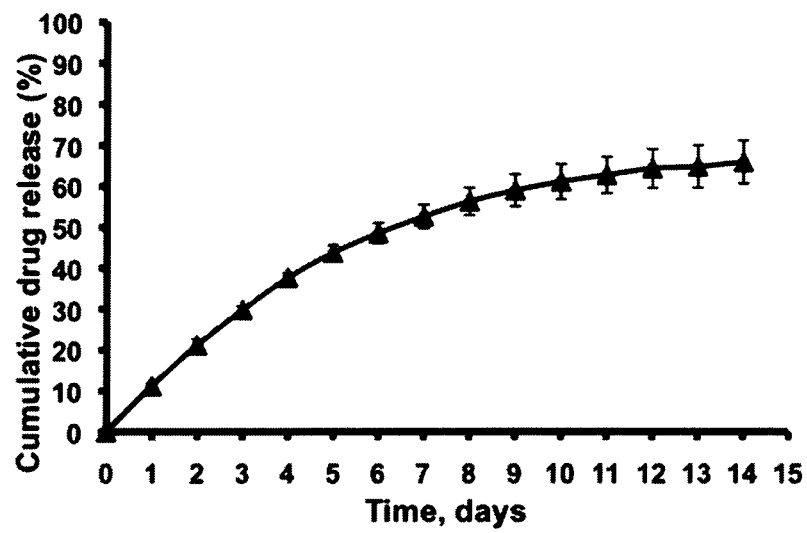
FIG. 1 shows a plot of in vitro dialysis release study of latanoprost from egg phosphatidyl choline (EPC) liposomes obtained after extrusion, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Various embodiments provide a liposomal formulation of ocular drug delivery, that is, drug delivery to an eye. The liposomal formulations having various drug-to-lipid mole ratios and encapsulating various compositions of prostaglandin drugs exhibit improved sustained release of the drugs from the liposomal formulations. Additionally, such liposomal formulations also circumvent the need of patient compliance under strict regime. For example, administering subconjunctival injections of sustained release of the drug loaded in liposomes exhibit excellent effectiveness of delivering superior therapeutic concentration of drug to the eye without the need to depend on patient compliance. Further, application of liposome delivery of drugs will extend to not only anti-glaucoma medications such as latanoprost but also to antibiotics and anti-inflammatory agents such as steroids.

In one aspect, the invention relates to a liposomal formulation for ocular drug delivery comprising (i) liposomes comprising at least one lipid bilayer, and (ii) a prostaglandin drug and/or a prostaglandin derivative associated in the liposomes, wherein the liposomes have a mean diameter of less than 2 μm.

In the context of various embodiments, the term "liposomal formulation" may mean a formulation of liposomes, wherein liposomes are artificially prepared vesicles made of lipid bilayer, which is defined as a thin membrane made of two layers of lipid molecules. Lipid bilayer may be in a form of a single or one lipid bilayer, or of multiple lipid bilayers. Liposomes may be filled or loaded with drugs, and used to deliver drugs for cancers and other diseases. The drugs may therefore be associated in the liposomes, wherein the term "associated" may generally refer to being coupled, connected, related, linked or encapsulated.

In various embodiments, the liposomes may comprise lipids selected from the group consisting of fatty acyls, glycerolipids, phospholipids, glycerophospholipids, sphingolipids, sterol lipids, preno lipids, saccharolipids, and polyketide lipids. For example, liposomes may be composed of naturally derived phospholipids with mixed lipid chains or other surfactants.

According to various embodiments, the glycerophospholipids may comprise phosphatidylcholines.

In the context of various embodiments, the term "phosphatidylcholines" may generally refer to a class of phospholipids (amphipathic lipids) that incorporate choline as a headgroup with one or more phosphate groups attached to it, and more specifically, refer to a lipid consisting of a glycerol bound to two fatty acids and a phosphate group. The term "lipid" may generally refer to an oily organic compound insoluble in water but soluble in organic solvents. For example, the phosphatidylcholines may be selected from the group consisting of 1,2-dioleoyl-sn-glycero-3-phosphocholines (DOPC), 1,2-dioleoyl-sn-glycero-O-ethyl-3-phosphocholines, 1,2-Dilauroyl-sn-glycero-3-phosphocholines (DLPC), 1,2-Dimyristoyl-sn-glycero-3-phosphocholines (DMPC), 1,2-Dipalmitoyl-sn-glycero-3-phosphocholines(DPPC), 1,2-Distearoyl-sn-glycero-3-phosphocholines (DSPC) and mixtures thereof. Phosphatidylcholines may be used alone or in combination.

In one embodiment, the phosphatidylcholines may be 1,2-Dipalmitoyl-sn-glycero-3-phosphocholines (DPPC).

The structure of DPPC is

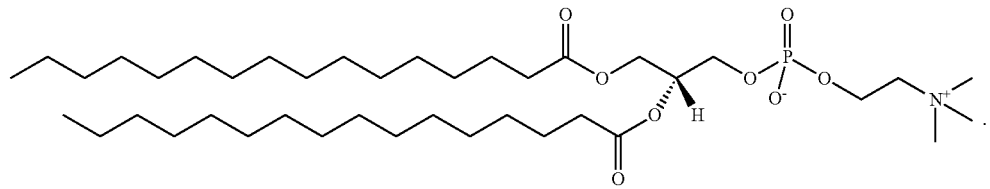 [SMILES: CCCCCCCCCCCCCCCC(=O)OC[C@H](COP(=O)([O-])OCC[N+](C)(C)C)OC(=O)CCCCCCCCCCCCCCC]

In various embodiments, the phosphatidylcholines may each comprise at least one unsaturated fatty acid moiety. For example, the phosphatidylcholines may each comprise L-α-phosphatidylcholine or 95% Egg phosphatidylcholines (EPC).

The structure of EPC is

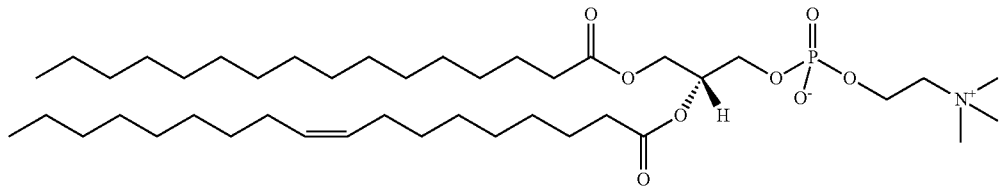

In various embodiments, the sphingolipids may each comprise at least one unsaturated fatty acid moiety. For example, the sphingolipids may each comprise hexadecanoylsphingomyelin or Egg Sphingomyelin.

In various embodiments, the prostaglandin drug and/or the prostaglandin derivative is encapsulated in the liposomes.

In the context of various embodiments, the term "prostaglandin drug" may generally refer to a drug that contains any member of a group of lipid compounds that are derived enzymatically from fatty acids and have important functions in the animal body. Every prostaglandin contains 20 carbon atoms, including a 5-carbon ring. A prostaglandin derivative forms the prostanoid class of fatty acid derivatives, for example, a subclass of eicosanoids.

The prostaglandin drug and/or the prostaglandin derivative used in ocular drug delivery may include a drug that is effective in preventing or treating a disease in the eye. The prostaglandin drug and/or the prostaglandin derivative may be for delivery to the eye. In various embodiments, the prostaglandin drug or the prostaglandin derivative may be selected from the group consisting of latanoprost, bimatoprost, travoprost, carboprosttrometamol, gemeprost, sulprostone, dinoprostone (PGE2), alprostadil (PGE1), beroprost, iloprost, epoprostenol, treprostinil, misoprostol, enoprostil, omoprostil, limaprost, unoprostone isopropyl, and arthrotec. Examples of the prostaglandin drug and/or the prostaglandin derivative may also include but not limited to carteolol hydrochloride, nipradilol, tafluprost, epinephrine, pilocarpine hydrochloride, acetazolamide, tiopronin, parotin, pirenoxine, glutathione, memantine, fluorometholone, dexamethasone, indomethacin, dichlofenac sodium, an agent for preventing or treating glaucoma, an agent for preventing or treating cataract, an agent for preventing or treating uveitis, an agent for preventing or treating diabetic retinopathy, an agent for preventing or treating age-related macular degeneration, an agent for preventing or treating vitreous opacity, an optic nerve protecting agent, and an angiogenesis inhibitor.

In various embodiments, the prostaglandin drug may comprise latanoprost.

Generally, there are three types of liposomes, namely multilamellar vesicles (MLV), small unilamellar vesicles (SUV) and large unilamellar vesicles (LUV).

Straight forward hydration of lipids produces MLVs. The MLVs may pass through filters, for example, polycarbonate filters having a filter pore size of about 2 µm. The MLVs obtained may have a size distribution of about 0.9-1.5 µm.

Unilamellar vesicles may be produced directly from MLVs by extrusion or sonication or, alternatively, may be obtained by reverse phase or detergent removal procedures. By extrusion, for example extruding 5 times through 0.2 µm polycarbonate filters, 5 times through 0.1 µm polycarbonate filters, and 10 times through 0.08 µm polycarbonate filters sequentially, the MLVs may be downsized to LUVs with a mean size or diameter of about 100 nm, for example 100±20 nm.

Sonication may be typically used to obtain SUVs.

SUVs may also be obtained by extrusion through filters, for example polycarbonate filters, with smaller pore sizes as compared to the case for LUVs.

LUVs are suitable for topical ocular delivery because they are optically clear and do not increase in size upon storage. It is important for a liposomal formulation to be optically clear for ocular drug delivery, especially for sustained release of ocular drug encapsulated in the liposomal formation so that clear vision and sight of the eye can be maintained throughout the administration process and the drug release process.

In various embodiments, the liposomes are small unilamellar vesicles (SUV) or large unilamellar vesicles (LUV) or multilamellar vesicles. In one embodiment, the liposomes may have a mean diameter of less than 1 µm. In yet another embodiment, the liposomes may have a mean diameter of about 100 nm to about 300 nm. For example, the liposomes may have a mean diameter of about 20 nm to about 50 nm. In context of various embodiments, the term "mean diameter" may generally refer to a mathematical average of a set of diameters, each diameter being taken for each liposome in a liposome population. The term "about" associated with the measure of a diameter may generally refer to an approximate which may be due to the imperfect circular structure of a liposome that may be elliptical in shape.

In various embodiments, the liposomal formulation has a drug to lipid mole ratio of about 0.01 to about 0.50. For example, the liposomal formulation may have a drug to lipid mole ratio of about 0.50 or about 0.18.

In various embodiments, the liposomal formulation has a polydispersity index of less than or equal to 0.25.

In the context of various embodiments, the term "polydispersity index" refer to a measure of the distribution of molecular mass in a given polymer sample, given by the ratio of the weight average molecular weight to the number average molecular weight.

The weight average molecular weight is calculated by $$\overline{M}_w = \frac{\sum_i N_i M_i^2}{\sum_i N_i M_i}$$

where Ni is the number of molecules of molecular weight Mi. The weight average molecular weight may be determined by light scattering, small angle neutron scattering (SANS), X-ray scattering, and sedimentation velocity.

The number average molecular weight is the ordinary arithmetic mean or average of the molecular weights of the individual macromolecules. It is determined by measuring the molecular weight of n polymer molecules, summing the weights, and dividing by n, given by $$\overline{M}_n = \frac{\sum_i N_i M_i}{\sum_i N_i}.$$

The number average molecular weight of a polymer may be determined by gel permeation chromatography, viscometry (Mark-Houwink equation), and all colligative methods like vapor pressure osmometry or end-group determination.

In one embodiment, the liposome further comprises cholesterol. For example, EPC may be with and without added cholesterol. The cholesterol may also include derivatives thereof, for example, cholestanol, dihydrocholesterol, cholesteryl esters, phytosterol, sitosterol, stigmasterol and campesterol.

Various amount of cholesterol may be comprised in the liposome. For example, the cholesterol may be of an amount of about 0% to about 50% by weight of the liposome, about 0% to about 40% by weight of the liposome, about 0% to about 30% by weight of the liposome, about 0% to about 20% by weight of the liposome, about 0% to about 10% by weight of the liposome, about 10% to about 50% by weight of the liposome, about 10% to about 40% by weight of the liposome, about 10% to about 30% by weight of the liposome, about 10% to about 20% by weight of the liposome, about 20% to about 50% by weight of the liposome, about 20% to about 40% by weight of the liposome, about 20% to about 30% by weight of the liposome, or about 30% to about 40% by weight of the liposome.

In one embodiment, the cholesterol may be of an amount of about 10% to about 40% by weight of the liposome.

In various embodiments, the liposome further comprises a linear $C_8$-$C_{20}$ alkyl or alkenyl amine. In the context of various embodiments, by "$C_8$-$C_{20}$ alkyl" is meant a straight chain hydrocarbon group having from 8 to 20 carbon atoms, and by "$C_8$-$C_{20}$ alkenyl" is meant a straight chain hydrocarbon group containing one or more double bonds and having from 8 to 20 carbon atoms. Linear $C_8$-$C_{20}$ alkyl or alkenyl amines include, without limitation, dodecyl amine, tallow amine, stearyl amine, cocoamine, octadecyl amine, N-octyloctan-1-amine, 2-nonenylamine, di(2-nonenyl)amine, and mixtures thereof, among others. These linear $C_8$-$C_{20}$ alkyl or alkenyl amines may be used alone or in combination. In one embodiment, the linear $C_8$-$C_{20}$ alkyl or alkenyl amine is stearyl amine. For example, DPPC may be with and without added stearyl amine.

Various amount of stearyl amine may be comprised in the liposome. For example, the stearyl amine is of an amount of about 0% to about 30% by weight of the liposome, about 10% to about 20% by weight of the liposome, about 0% to about 10% by weight of the liposome, or about 20% to about 30% by weight of the liposome.

In one embodiment, the stearyl amine may be of an amount of about 5% to about 25% by weight of the liposome. In yet another embodiment, the stearyl amine is of an amount of about 10% to about 20% by weight of the liposome.

In another aspect, the invention relates to a pharmaceutical composition comprising the liposomal formulation. The pharmaceutical composition may be in a form of an ophthalmic solution. In various embodiments, the pharmaceutical composition is for use in ocular drug delivery in a form of an eye drop, or an injection, or a viscous aqueous vehicle. In another embodiment, the viscous aqueous vehicle comprises an aqueous solution of polysaccharides. The polysaccharides may be hyaluronic acid. By applying the liposomal formulation using the viscous aqueous vehicle, the liposomal formulation may retain in the eye for longer without clearance.

In yet another aspect, the invention relates to a method of producing the liposomal formulation of the ocular drug by thin-film hydration technique. Thin-film hydration technique enables uniform encapsulation of drug, in this case, ocular drug within the phospholipids of the liposomal formulation. In the context of various embodiments, the technique of thin-film hydration generally refers to a technique that is performed by firstly dissolving basic components forming a liposome membrane in an organic solvent such as chloroform, secondly subsequently subjecting the solution to a rotary evaporator to distill off the solvent by heating under reduced pressure to form a thin film on the inner side of the evaporator, and thirdly hydrating the thin film with a phosphate buffer solution, or a HEPES-HBSS solution in a warm water bath. When the drug is water-soluble, it is dissolved in a solution for hydration, and when the drug is water-insoluble, it is dissolved in an organic solvent together with the liposome-forming components. In various embodiments, the method may further comprise downsizing the liposomal formulation by extrusion through a filter or by sonication.

In yet another aspect, the invention relates to a method for treating or preventing an ocular disease, comprising administering the liposomal formulation or the pharmaceutical composition to a subject in need thereof. Examples of ocular diseases include but not limited to glaucoma, cataract, uveitis, vitreous opacity, diabetic retinopathy, age-related macular degeneration. In various embodiments, the ocular disease is glaucoma.

In various embodiments, the method comprises administering the liposomal formulation or pharmaceutical composition by subconjunctival injection to provide sustained release of the ocular drug. By applying the liposomal formulation via injection into the conjuctival sac, there may be provided a greater retention of the liposomal formulation in the eye.

In order that the invention may be readily understood and put into practical effect, particular embodiments will now be described by way of examples and not limitations, and with reference to the figures.

EXAMPLES

Latanoprost is successfully loaded into DPPC, egg phosphatidylcholine (EPC) and DMPC liposomes. The loading of latanoprost into such liposomes is unexpected found to be substantially higher than is possible with drugs of a similar nature. Latanoprost has selective affinity for certain liposomes, and this is responsible for the high drug loading, and extended release obtainable from the liposomal formulations, as illustrated by way of examples in the following:—

Example 1

Evaluating a Liposomal Formulation for Sustained Release of Latanoprost in a Rabbit Model Example 1

Materials

Egg phosphatidylcholine (EggPC) is purchased from NOF Corporation, Japan. Polycarbonate filters membranes of sizes (0.2, 0.1 and 0.08 µm) and drain discs are purchased from Northern Lipids Inc, Canada. Cellulose ester dialysis bags (16 mm dia×10 m flat width) are obtained from Spectrum labs, USA. Chemicals for phospholipid analysis such as ammonium thiocyanate and ferric chloride hexahydrate are purchased from Sigma, USA. Sodium phosphate dibasic anhydrous ($Na_2HPO_4$), Potassium phosphate monobasic anhydrous ($KH_2PO_4$), Potassium chloride (KCl), Sodium chloride (NaCl) salts are purchased from Sigma, USA and used without further purification. Latanoprost is purchased from Chemical Testing and Calibration Laboratories, China. The water used in all the experiments is from MiliQ purification system with a resistivity of at least 18.2±0.2 mΩ cm. All solvents for drug estimation are carried out using high performance liquid chromatograph (HPLC) grade (>99% purity) and are purchased from Tedia, USA.

Example 1

Methods

Preparation of Large Unilamellar Vesicles (LUVs)

A thin film hydration technique is used to formulate latanoprost loaded EggPC liposomes. Briefly, known amounts of phospholipid; EggPC (lipid concentration, 18 mM) is weighed and dissolved in chloroform:methanol (2:1, v/v) solvent mixture. A known volume of the drug solution of latanoprost (2 mg/ml stock solution in acetonitrile) is added to the lipid solvent mixture maintained at 40° C. An initial drug:lipid molar ratio of 0.154 may be used. The solvent mixture is removed from the round bottom flask using a rotary evaporator (IKA RV 10, Germany) connected to a water bath (IKA MB 10 basic, Germany) maintained at 40° C. To completely eliminate any trace of residual solvent, the flask is rotated at 100 rpm, under low pressure for an hour. A thin drug loaded lipid film is obtained and to this film, isotonic PBS (150 mM, pH 5.5) buffer is added to form Multilamellar Vesicles (MLVs). Subsequent size reductions may be carried out by sequential extrusion of MLVs (10 times) through polycarbonate filters of size (0.2 μm/0.08 μm), fitted in a bench top extruder that is purchased from Northern Lipids Inc, Canada. At the end of this step, large unilamellar vesicles (LUVs) with a size distribution of 0.09-0.12 μm are obtained. All of the above-mentioned steps are performed under aseptic conditions. All glassware, PBS (filtered through 0.2 μm filter) solution are sterilized by autoclaving, and the entire procedure is performed under a laminar flow hood (ESCO, Singapore).

Characterization of Drug Loaded EggPC Liposomes

Size and Zeta Potential

The average size of the liposomes as well as the size distribution (polydispersity index, PDI) is carried out using the Malvern Zetasizer Nano ZS (UK). The vesicle sizes are continuously monitored following preparation, on storage (4° C. and 25° C.) and after drug release in vitro.

Lipid Analysis

The phospholipid concentration is estimated using colorimetric method. The amount of phospholipids after extrusion is estimated to be around 80-85% (by mass).

Estimation of Drug Concentration Using High Performance Liquid

Chromatography Method

The concentration of the latanoprost is estimated using a HPLC system (Agilent series 1200). The chromatographic separation is performed on reverse phase Eclipse-XDB C18 column (5 μm, 4.6 mm ID×250 mm) using mobile phase as ACN: Water at 70:30 (v/v) proportions. The flow rate is maintained at 1.0 ml/min and wavelength is set at $\lambda=210$ nm. The retention time is 4.3 mins and the temperature of the column is maintained at 25° C. The released latanoprost concentration may be estimated directly from the collected samples in PBS pH 7.4. The total drug concentration may be estimated by breaking the liposomes in a solvent system, such as isopropyl alcohol in a volume ratio of 1:4. The broken lipid mass may then be centrifuged and isolated from the rest of solution by ultracentrifugation at 13000 rpm for 30 mins. The supernatant may be diluted 50× times with PBS pH 7.4 and analyzed for total drug concentration. The total and released drug values may be estimated in comparison with a standard calibration curve of latanoprost in PBS pH 7.4. The drug loading efficiency is calculated as follows:

Drug loading efficiency (%)=100×(Amount of drug retained/Amount of drug taken initially)

Drug Partition Coefficient Estimation

The values for partition coefficient are estimated from the MLVs prior to the extrusion step. Briefly, known sample volumes are collected in microfuge tubes and centrifuged at 10000 rpm for 30 mins. The drug estimated from the supernatant is a measure of continuous (buffer) phase drug concentration, while this amount when subtracted from the total drug concentration yields drug partitioned into the bilayer. Thus, drug partition coefficient (P.C.) is estimated using the following expression (each concentration in mass per unit volume):

P.C.=(Total amount of drug−amount of drug in buffer)/amount of drug in buffer

The final drug: lipid ratios in the liposomal formulation obtained after extrusion may be estimated as follows:

Final drug to lipid (D/L) mole ratio=moles of drug left/moles of the lipid left after extrusion Drug Release Studies A dialysis method is followed to evaluate the release of latanoprost from EggPC liposomes. Briefly, 1 ml of drug loaded liposomal suspension is taken in a cellulose ester dialysis bag (100 kD MWCO, 1.6 cm dia×6 cm length) and dialyzed against 40 ml of PBS pH 7.4. The dialysis bag may be continuously agitated in an orbital shaker (Sartorius Cartomat, USA) maintained at 37° C. at 50 rpm. To maintain dynamic sink conditions similar to in-vivo, the dialysate is completely exchanged with fresh PBS pH 7.4 buffer every 24 hours. Aliquots are withdrawn from the release medium and are filtered through 0.2 μm syringe filter and assayed for release drug. The volume of liposomes and sizes of vesicle in the dialysis tube are recorded at the end of release study to check for any dilution effect and/or size change of vesicle.

Estimation of Latanoprost in Ocular Fluids (Aqueous and Vitreous Humour)

The aspirated aqueous and vitreous humours are collected in sterile 1 ml syringes. The humours are directly filtered through 0.2 μm sterile syringe filters (regenerated cellulose) into microfuge tubes. The samples in the microfuge tubes are then vortexed and ultra-centrifuged at 13000 rpm for 15 mins to remove any particulates/debris. The supernatant may then be aspirated into a syringe and transferred into amber colored HPLC vials with insets. The latanoprost amount in these fluids is estimated by HPLC method as earlier described, using the volume of aqueous humour as 0.15 ml and vitreous humour as 0.3 ml from a rabbit eye.

In Vivo Studies in the Rabbit Eye

Sixteen female New Zealand White rabbits are used in this study. The baseline IOP is measured twice daily using a calibrated Tono-pen XL (Reichert Ophthalmic Instruments, Depew, N.Y., USA) for 7 days in all rabbits. The rabbits are divided into 2 treatment groups: (i) Group A (8 rabbits, 16 eyes) has received 1 subconjunctival injection of latanoprost-loaded liposomes using a 27 gauge needle; (ii) Group B (8 rabbits, 16 eyes) has received 1 eye drop of topical latanoprost daily. All procedures are performed under topical anesthesia (amethocaine 2.5%) by a single surgeon (MA). In brief, the eyes are first cleaned with 50% povidone iodine and 0.1 ml of liposome formulation is injected in the subconjunctival space in the superior temporal region of each eye. Topical chloramphenicol 2.5% is administered to the operated eye daily for 5 days. Approval has been obtained from the SingHealth Institute Animal Care and Use Committee and all procedures have been performed in accordance with the ARVO Statement for the Use of Animals in Ophthalmic and Vision Research.

Clinical Evaluation, Slit-Lamp Microscopy, Anterior Segment Imaging

Twice-daily IOP measurements are conducted using a calibrated Tono-pen XL and visual inspection of all eyes following injections or topical latanoprost for signs of conjunctival irritation, inflammation or infection at the injection site. Slit-lamp examination of the exterior and anterior chamber of the eyes is performed prior to the injections and weekly thereafter. Anterior segment photographs and anterior segment optical coherence tomography (AS-OCT) of the eyes that received the liposome formulation are performed at weekly intervals. The rabbits are also monitored for any gross changes such as eye discharge, squinting or abnormal behavior. A modified Hackett McDonald ocular score is used to grade conjunctival injection, conjunctival swelling, discharge, corneal clarity and aqueous flare.

Histology

At the end of the study period (90 days) all rabbits have been sacrificed and aqueous and vitreous humor for latanoprost concentrations are sampled via HPLC analysis. Euthanasia may be carried out with intraperitoneal pentobarbitone (60-150 mg/kg) followed by enucleation of the eyes. Sterile syringes with 27-gauge needles are used to sample 0.1 ml of aqueous humor and 0.1 ml of vitreous humor before immediately immersing the eyes in a mixture of 4% paraformaldehyde and 2.5% neutral buffered formalin for 24 hours. The dehydrated globes are embedded in paraffin and sent for microtome sectioning and staining (Haematoxylin and Eosin, H&E).

Statistical Analysis

Statistical analysis included descriptive statistics, where the mean and standard deviation (SD) is calculated for the continuous variables; while frequency distribution and percentages are used for categorical variables. Comparisons between categorical variables are conducted by Fisher's exact tests, whereas the one-way analysis of variance (ANOVA) test is used for means. A P-value <0.05 is considered statistically significant.

Experimental Data

Drug Loading Efficiency

The particle size of latanoprost loaded EggPC liposomes are in the nano-size range (Z avg=109±18), with a narrow polydisperisty index (0.19±0.04). A high loading efficiency of latanoprost in EggPC liposomes is achieved (94±5%) for an initial drug/lipid mole ratio of 0.154. The final latanoprost concentration in EggPC liposomes after extrusion is estimated to be greater than 1 mg/ml which is 20 fold higher than commercially available topical latanoprost (50 µg/ml) which is administered daily. The final drug/lipid mole ratio value is estimated to be 0.181. The reason for the higher final value of drug/lipid mole ratio may be due to more partial loss of lipids during extrusion.

In Vitro Size Stability

The changes in the size of the liposomes on storage and as well on release are continuously monitored in a Zetasizer at various temperatures conditions. As shown in Table 1, the EggPC vesicles have a significant change in the vesicle size and polydisperisty when compared to latanoprost loaded EggPC liposomes.

TABLE 1

Size measurement of liposomes during storage at 4° C., 25° C. and after drug release in PBS buffer (pH 7.4) at 37° C.

| | Size measurement, nm (PDI) | | | | | |
|---|---|---|---|---|---|---|
| | Temperature (° C.) | | | | | |
| | 4° C. | | | | 25° C. | |
| Type of liposome | 0 | Duration (months) 1 | 2 | 6 | Duration (months) 1 | After in-vitro drug release 37° C. |
| EPC liposome | 79.8 (.09) | 114.4 (0.19) | 180.3 (0.34) | 1200 (0.46) | NA | NA |
| Latanoprost loaded EPC liposomes | 86.6 (0.17) | 83.91 (0.14) | 89.98 (0.14) | 86.38 (0.11) | 82.88 (0.18) | 82.02 (0.08) |

Micron sized particles may be observed within six months on storage at 4° C. for liposomes without any drug. However, the data for latanoprost loaded EggPC liposomes shows that the liposomes are stable for at least six months on storage at 4° C. and at least for a month at 25° C.

In-Vitro Drug Release from EggPC or EPC Vesicles

The release of latanoprost from the liposomes is evaluated by a dialysis technique and expressed in terms of cumulative drug release (%) over time as shown in FIG. 1. In FIG. 1, the cumulative latanoprost release (%) from EggPC liposomes is plotted against time (days) for a drug/lipid mole ratio of 0.181. Each value is plotted as the average of the results obtained from three independent experiments. The standard deviation is plotted as error bars, which is less than 4%. A slow and sustained release of the drug is achieved with 60% of the drug being released at the end of two weeks in in vitro conditions. In addition, the size changes are minimal at the end of the in-vitro drug release (Table 1).

Figure 2:
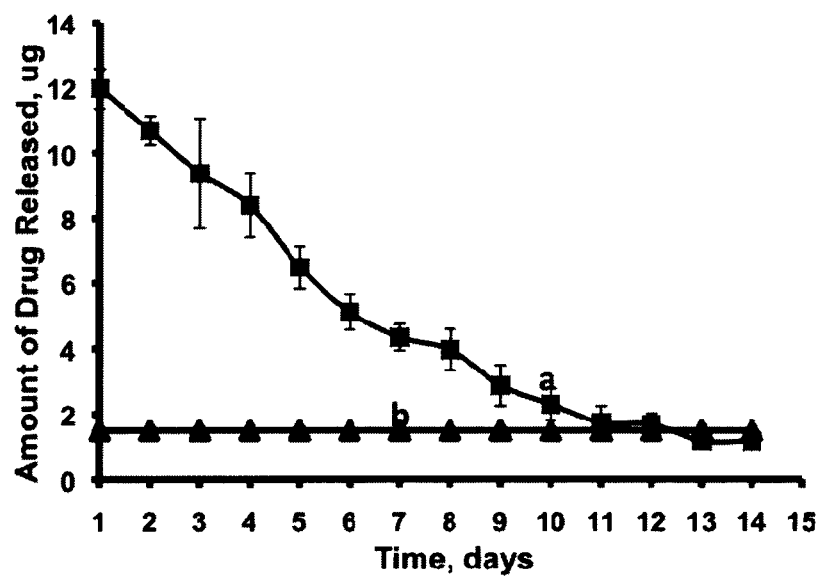
FIG. 2 shows a plot illustrating latanoprost release rate, according to various embodiments.

Based on the data derived from loading, release and stability studies, the efficacy of IOP lowering from latanoprost-loaded EggPC liposomes (D/L mole ratio of 0.181) in rabbit eyes is investigated. The selection rationale is based from studies made on DPPC liposomes (Example 3), with an injection volume of 100 µL. The dose/day is targeted for at least two weeks similar to that of topical latanoprost (1.5 µg/drop/day). The actual drug amounts released from EggPC liposomes is compared to topical latanoprost formulation as shown in FIG. 2. In FIG. 2, Latanoprost release rate is from 100 µl of EggPC liposome with a drug/lipid mole ratio of 0.181 compared with 1 drop of once-daily topical latanoprost, i.e., commercial Xalatan® solution (1.5 µg/drop). The release rates are based on average values of at least two batches and standard deviations are shown in error bars. The ratio of the drug concentration in the lipid phase to that in the continuous phase determines the partition coefficient (P.C.). A partition coefficient value of 28±5 is estimated for EggPC liposomes. This value translates to greater than 95% of the drug in associated/entrapped within the lipid bilayer.

Results of In Vivo Study

A. Intraocular Pressure

Figure 3:
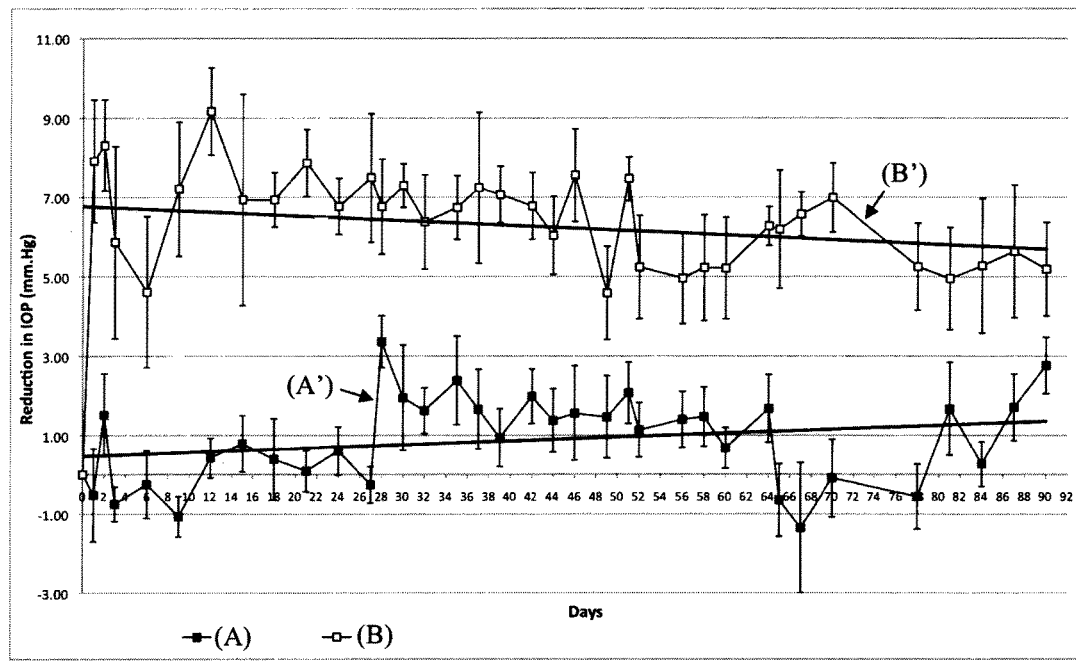
FIG. 3 shows a plot of in vivo intraocular pressure recordings (reduction in intraocular pressure compared to baseline) comparing the liposome-loaded latanoprost group to the control group (once-daily topical latanoprost), wherein (A) refers to a control, (B) refers to a latanoprost-loaded liposome, (A') refers to linear(control) and (B') refers to linear(latanoprost-loaded liposome), according to various embodiments.

The baseline IOP is 13.6±0.3 mmHg for all 16 rabbits and there is no significant difference between the 2 groups (P=0.80). A significantly higher mean reduction of IOP in the subconjunctival latanoprost-loaded liposome group compared to the topical latanoprost eye drop group, which is maintained for 90 days (4.8±1.5 vs. 2.5±0.9 mmHg; P<0.001) is as shown in FIG. 3. In FIG. 3, there are significant differences in intraocular pressure readings throughout the 90-day study period.

B. Modified Hackett-Macdonald Scores

The Modified Hackett-Macdonald Scores of the injection site are determined by calculating the percent increase in score from pre-injection to the end of the study (90 days) in each treatment group. There is no significant difference in the scores comparing both treatment groups (10±0.5% vs. 12±0.6%; P=0.32). No complications such as conjunctival infections or anterior chamber inflammation on slit-lamp examination are also observed.

C. Anterior Segment Optical Coherence Tomography (ASOCT) and Histology

Figure 4:
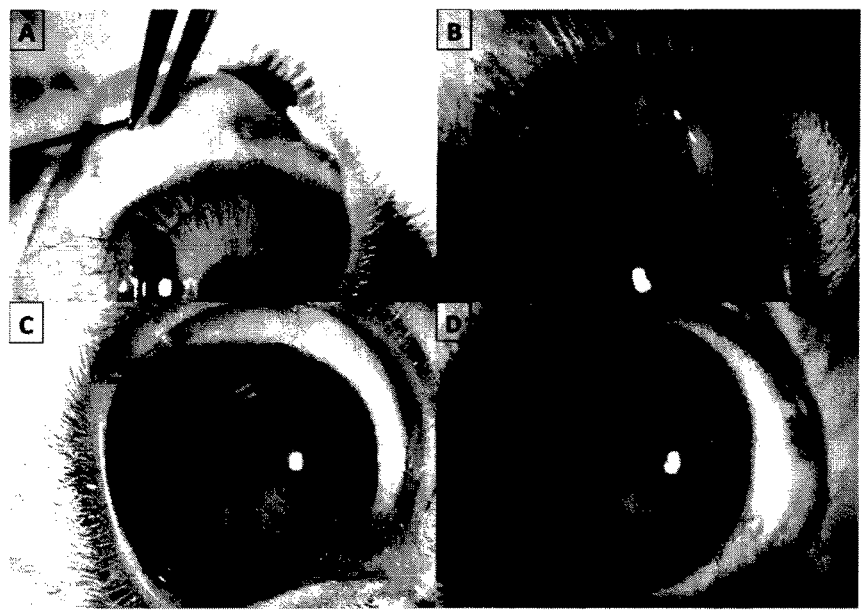
FIG. 4 shows photo images of A: Injection of subconjunctival liposome formulation, B: Immediate post-injection of liposome formulation, C: Slit-lamp photograph of eye post-injection at Day 90, and D: Slit-lamp photographs of eye receiving one drop of topical latanoprost daily at Day 90.
Figure 5:
FIG. 5 shows an anterior segment optical coherence tomography (A) confirming the subconjunctival location of the liposome formulation immediate post-injection, and (B) no evidence of scleral thinning or conjunctival scarring at Day 90.

ASOCT scans confirm subconjunctival location of liposomes in the superior temporal aspect of each rabbit eye just after injections as shown in FIG. 4. Subsequent ASOCT scans performed do not reveal any abnormal scarring or scleral thinning at the injection sites as shown in FIG. 5.

It is shown that a single subconjunctival injection of latanoprost-loaded EggPC liposomes may effectively lower the IOP in rabbit eyes for at least 90 days. This IOP-lowering effect is significantly greater than once-daily topical latanoprost, the current 'standard of treatment' in glaucoma patients. These observed results are also consistent with our in vitro results, which demonstrate a slow and sustained release of latanoprost, with stability in liposome size and structural integrity. The sustained reduction of IOP in rabbit eyes is encouraging, and there appears no other reports to date that show such a significant effect of latanoprost sustained-release via liposomes in the animal eye. The liposome formulation is demonstrated to be well tolerated as evidenced from the lack of recorded ocular irritation or inflammation.

A nano-sized liposomal formulation with a narrow polydisperisty is developed, and a high final Drug/Lipid (D/L) mole ratio of 0.181 using EggPC liposomes is achieved. While a similar high D/L mole ratio for other lipophilic drugs such as paclitaxel (0.15), 17 aryl-imidazole compound (ML220) (0.29), 18 and curcumin (0.07) 19 have been reported, the D/L mole ratio for hydrophobic drugs such as ibuprofen (0.02) 20 and cisplatin (0.05) are comparatively low. A maximum D/L mole ratio of 0.104 using DPPC liposomes, synthesized from a saturated lipid that maintained an IOP lowering effect for 50 days in the rabbit eye may also be achieved. Hence, this is a significantly improved formulation in terms of the D/L mole ratio using EggPC with a longer IOP lowering effect in the same species.

Storage stability analysis shows that liposomes (without latanoprost) increased to micron size particles within six months of storage at 4° C. This is consistent with previously reported studies with EggPC liposomes. However, notable disintegration is usually observed for hydrophobic drug-loaded liposomes, hence limiting its potential for a sustained drug delivery. Latanoprost-loaded liposome formulation has minimal size changes detected at both 4° C. (>6 months) and 25° C. (>1 month). This suggests that latanoprost does not destabilize the bilayer of EggPC liposomes, and may even help to improve the stability under storage conditions, similar to the effects of cholesterol. This is further supported by similar stability of high-loading curcumin into EggPC and paclitaxel into mixed liposomes composed of saturated and unsaturated lipids.

Ideally, a topical formulation using drug-loaded liposomes with superior drug-effects may be developed to replace topical eyedrops. However, the major limitation with topical liposomes is the lack of sustained efficacy, due to biological barriers in the eye and clearance from tear dilution. Different routes of injectable liposome systems tested include periocular, intravitreal and subconjunctival. Moreover, the benefits of subconjunctival injections have been shown with improved absorption rates and sustained efficacy, using low molecular weight heparin, streptokinase and clodronate. It is shown in Example 1 that the subconjunctival delivery of liposomes can clearly bypass these barriers thereby allowing these nanoparticles to be potentially used as a platform for sustained release of drugs.

A previous study has suggested that the liposomes behave like a depot system in the subconjunctival space. It has been explained that there may be a lack in systemic clearance of liposomes and remain at the site of injection probably due to larger particle size (~550 nm) of the liposomes. However, it is now demonstrated that there is considerable success in attaining sustained reduction in IOP over an extended time frame of 90 days from a single injection. It is also now demonstrated the safety of this liposome injection in the rabbit eye.

Example 2

Determining the Effect of Cholesterol on EPC Liposome

Example 2

Materials

Ocular drug: Latanoprost

Phospholipids: EPC (Sample 6-a), EPC with cholesterol of an amount of 10% by weight of the liposome (Sample 6-b), EPC with cholesterol of an amount of 20% by weight of the liposome (Sample 6-c)

Liposomal formulations of ocular drug having drug to lipid mole ratio of about 0.1.

Example 2

Procedure

Similar procedure as for Example 1 is used. To obtain the various samples, the EPC in Example 1 may be replaced with EPC with added cholesterol of different amounts of 10%, and 20% by weight of the liposome.

Figure 6:
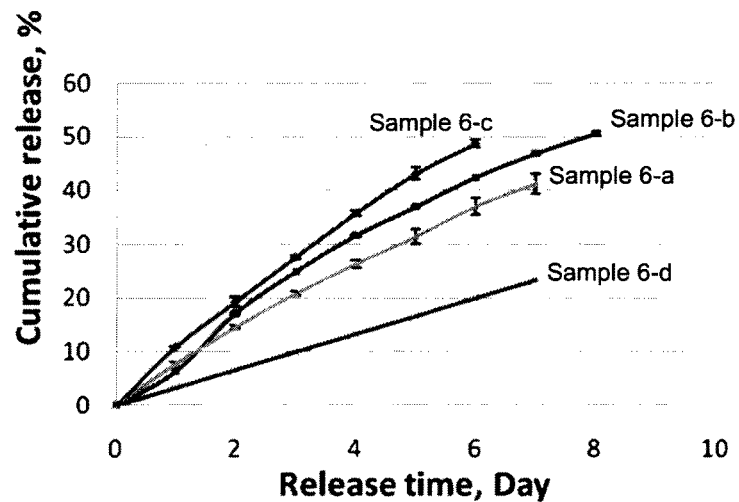
FIG. 6 shows a plot of drug-release curves for liposomal formulations involving egg phosphatidyl choline (EPC) according to various embodiments.

FIG. 6 shows the release curves of latanoprost from EPC SUVs with and without added cholesterol. The vertical Y-axis of the plot in FIG. 6 labeled as "cumulative release, %" refers to the percentage of the amount of drug being released from liposomal formulation over the total amount of drug contained in the liposomal formulation. The horizontal X-axis of the plot in FIG. 6 labeled as "release time, day" refers to the $n^{th}$ day of monitoring the drug release where n is 0, 1, 2, 3, 4, 5, 6, 7, . . . The desired rate for latanoprost release (Sample 6-d) is also included in FIG. 6 for comparison purposes. This desired rate reflects the rate at which latanoprost is released based on an eye drop formulation. In FIG. 6, the error bars shown refer to standard deviations.

In FIG. 6, it is shown that the addition of cholesterol to EPC gives average release rates higher than the desired release rate for latanoprost based on an eye drop formulation. Further, increasing average release rates is observed with increasing amount of cholesterol comprised in the liposomes. Average release rate mentioned herein refers to the gradient of the release curve over a period of more than 1 day of release time or over the total release time. An estimate may be obtained by approximating the release curve to a linear plot.

In FIG. 6, it is also shown that the addition of cholesterol to EPC gives daily release rates similar to or higher than the desired daily release rate for latanoprost based on the eye drop formulation. More specifically, higher daily release rates of about 6% to 10% are observed for the liposomal formulations as compared to that of the eye drop formulation, which has a daily release rate of about 4% for the period between the $0^{th}$ and $4^{th}$ day of release, while similar daily release rates of about 4.5%±0.5% are observed for the period between the $5^{th}$ and $7^{th}$ day of release. Daily release rate mentioned herein refers to the gradient of the release curve between the $n^{th}$ day and the $(n+1)^{th}$ day.

From FIG. 6, it can be concluded that the addition of cholesterol to EPC stabilizes the liposomal formulation and promotes sustained release of latanoprost. In Example 1, all samples of different liposomal formulation (i.e., Samples 6-a to 6-c) are optically clear with good size stability over time of storage. Similar observations on the trends of average release rates and daily release rates are made for liposomal formulations for ocular drug delivery having a drug-to-lipid mole ratio of about 0.01 to about 0.5, and having cholesterol of an amount of about 10%-40% by weight of the liposome.

Example 3

Evaluating Carrier Stability, Drug Partitioning, In Vitro Drug Release, Toxicity, Efficacy and Sustainability of Latanoprost-Incorporated DPPC Liposomes Upon Subconjunctival Administration in Rabbit Eyes Example 3

Materials'

DPPC is purchased from NOF Corporation, Japan. Cellulose ester dialysis bags (16 mm dia×10 m flat width) are obtained from Spectrum labs, USA. All other materials are prepared as in Example 1.

Preparation of Large Unilamellar Vesicles (LUVs)

Latanoprost loaded liposomes are formulated by thin film hydration technique. Briefly, known amount of DPPC (lipid concentration, 15 mM) is weighed and dissolved in chloroform:methanol (2:1, v/v) solvent mixture. A known amount of drug dissolved in acetonitrile (ACN) is added to this mixture and maintained in a 40° C. water bath. The drug: lipid mole ratios are varied between 0.04 to 0.24. Solvents are removed from the round bottom flask using a rotary evaporator (IKA RV 10, Germany) maintained in a 40° C. water bath (IKA MB 10 basic, Germany). A thin dry drug loaded lipid film is obtained and to this film, isotonic PBS (150 mM, pH 5.5) buffer is added and sonicated for 3-5 mins, to form multilamellar vesicles (MLVs). A longer exposure time to ultrasound is avoided, due to possibilities of increased lipid oxidation and/or drug leakages. After the completion of the sonication step, the resulting formulations are extruded 10-15 times sequentially through polycarbonate filters of size (0.2 μm/0.1 μm/0.08 μm), fitted in a bench top extruder (Northern Lipids Inc, Canada). This will result in formation of LUVs with a size distribution of 0.09-0.12 μm. All the above-mentioned steps are performed under aseptic conditions. All glassware, PBS (filtered through 0.2 μm filter) solution are sterilized by autoclaving, and the entire procedure is performed under a laminar flow hood (Esco, Singapore). Sterility (Method suitability test and Sterility test) conditions of the drug loaded formulations are verified through an external agency (BRASS, Biomedical Research and Support Service Pvt. Ltd., Singapore) and found to meet the desired criteria.

Example 3

In Vivo Study in Rabbits

Topical Application of Liposomal Formulation as Eye Drop

Six female New Zealand white rabbits are divided into two treatment groups. Daily IOP values are monitored and stable IOP baseline values are observed by the end of seven days. One treatment group (3 rabbits, 6 eyes) receives one daily drop of liposomal formulation and the other treatment group receives a drop of Xalatan® formulation (3 rabbits, 6 eyes).

Subconjunctival Delivery of Latanoprost Loaded Liposomes

Twenty three female New Zealand White rabbits (both eyes, BE=46 eyes) are used in this study. The baseline IOP is measured twice daily using a calibrated Tono-pen XL for 7 days in all rabbits. The rabbits are divided into 3 treatment groups: (i) Group A (8 rabbits, 16 eyes) receives 1 eye drop of topical latanoprost daily; (ii) group B (8 rabbits, 16 eyes) receives 1 subconjunctival injection of latanoprost-loaded liposomes and (iii) group C (7 rabbits, 14 eyes) receives subconjunctival injection of liposomes only (with no drug). Rabbit eyes in groups B and C receive a subconjunctival injection of liposomes at day 0 and at day 50 using 27 gauge sterile needles, since the IOP returns to the baseline values. All procedures are performed under topical anesthesia (amethocaine 2.5%) by a single surgeon (MA). In brief, the eye is cleaned with 50% povidone iodine and 0.1 ml of liposome is injected in the subconjunctival space in the superior temporal region of each eye. Topical chloramphenicol 2.5% is administered to the operated eye daily for 5 days. Approval has been obtained from the SingHealth Institute Animal Care and Use Committee and all procedures are performed in accordance with the ARVO Statement for the Use of Animals in Ophthalmic and Vision Research.

Clinical Evaluation

As per in Example 1. Further, a modified version of the Moorfields bleb grading system to objectively assess vascularity in all eyes is used.

Histology

At the end of the study period (80 days) all rabbits are sacrificed and sampled aqueous and vitreous humor for latanoprost concentrations via HPLC analysis. As per in Example 1. Further, polarization microscopy of stained collagen fibers is able to reveal any gross collagen bundling patterns and a modified semi-quantitative grading system to assess fibrosis and scarring.

Statistical Analysis

As per in Example 1.

Characterization of Drug Loaded Liposome Vesicles

Size and Zeta Potential

The average size of the liposome vesicles as well as the size distribution (polydispersity index, PDI) of each formulation is estimated using the Malvern Zetasizer Nano ZS (UK). A small aliquot of the formulation is diluted with a large (1:100, v/v) volume of distilled water and any air drop interference while measurement is eliminated all throughout the measurement. Vesicle sizes are monitored following synthesis, on storage at 4° C. and after drug release. The zeta potential values are estimated by Laser Doppler method using the same instrument in 0.001 M PBS buffer at 25° C. DPPC lipids is ensured that more than 75% of latanoprost is entrapped into the liposome while measurement. As indicated in Table 1, there is no appreciable change in particle size, zeta potential, although entrapment efficiency is noted to be slightly higher with lower drug/lipid mole ratio.

TABLE 1

Size, Zeta potential and loading efficiency of latanoprost loaded DPPC Liposome after extrusion.

| DPPC Liposomes (D/L, mole/mole) | Size (nm) | PDI | Zeta potential (mV) | Drug Loading Efficiency (%) |
|---|---|---|---|---|
| 0.04 | 90 ± 10 | 0.09-0.12 | −4.6 ± 2.0 | 85 ± 3% |
| 0.104 | 120 ± 20 | 0.1-0.2 | −7.1 ± 2.2 | 80 ± 5% |

Lipid Analysis

The phospholipid concentration is estimated using colorimetric method. Six point calibration is prepared for DPPC ($\lambda$max=525 nm) and are later used for estimation of unknown concentration of lipids in vesicles obtained after extrusion. The amount of phospholipids in liposomal vesicles after extrusion is estimated to be 80-85% (by mass) while, the remaining is considered lost while extrusion and handling.

DSC Analysis of the Drug and DPPC Interaction

DSC analysis of the latanoprost loaded DPPC liposome formulations is done using TA instruments Q10 model. The instrument Q10 model is calibrated with Indium for the best Cp estimate and high signal to noise ratio. Number of heating/cooling cycles, heating rate, volume of liposome formulation, and concentration in DI water/PBS buffer are all established by comparing the standard DSC chromatograms available for DPPC and its variation with cholesterol mole %. The DSC chromatograms obtained from Q10 undoubtedly need higher lipid mass compared to nano DSC, but the nature of DSC chromatograms are the same. A heating rate of 1° C./min between temperature ranges −20° C. to 60° C. is selected to avoid any thermal decomposition of drug molecule. A third heating cycle is always considered for all DSC analysis. The results are reproducible for 100 mg/ml liposomal formulations and a sample volume of 10 µl is taken in a hermitic pan for analysis. An empty pan is used as a reference.

Drug concentration using High Performance Liquid Chromatography Method

The HPLC system (Agilent series 1200) consists of solvent degasser, high precision pump, auto sampler, column heater, column, and a photo diode (UV) array detector. Each unit is interfaced with computer through Chemstation software. The chromatographic separation is performed on reverse phase Eclipse-XDB C18 column (5 µm, 4.6 mm ID×250 mm) using mobile phase as ACN:Water at 70:30 (v/v) proportions at 1.0 ml/min flow rate and detector wave length is set at $\lambda$=210 nm. The retention time is 4.6 mins and the temperature of the column is maintained at 25° C.

The drug estimation from release medium is done directly from the collected samples. While, the drug present in the lipid vesicles needs a separate treatment. Lipid vesicles of drug loaded formulation are broken by adding 1:4 volumes of IPA (isopropyl alcohol) and the lipid mass is isolated from the rest of solution by ultracentrifugation at 13000 rpm for 30 mins. The supernatant is diluted 50× times with PBS buffer to match within the calibration limit. HPLC system is calibrated ($R^2$=0.998) using known concentrations of latanoprost solution (25, 10, 7.5, 5, 2.5, 1.0, 0.1 µg/ml) by diluting known mass of latanoprost in ACN in PBS buffer (150 mM, pH 7.4). The estimation of the total drug is carried out by breaking the liposomal vesicles with IPA. The broken liposomal mixture is centrifuged and the clear supernatant is diluted with PBS buffer and estimated by HPLC. Each sample is tested at least five times to obtain concordant data of the total drug concentration of stock liposomal formulations. Amount (%) of drug released at various time are plotted against time.

Drug loading efficiency (%)=100×(Amount of Drug retained/Drug taken initially)

Drug Partition Coefficient Estimation

As per in Example 1.

Drug Release Studies

The drug loaded liposomal formulation is physically separated from the receptor chamber by a dialysis membrane and the released drug amounts are assayed from the release medium at various time intervals. Briefly, 1 ml of drug loaded liposomal suspension is taken in a cellulose ester dialysis bag (100 kD MWCO, 1.6 cm dia×6 cm length) and clipped at both ends using dialysis clips. The whole assembly is then placed in screw capped bottle (to avoid evaporation loss during the whole duration of release study) containing 40 ml PBS buffer (150 mM, pH 7.4: 137 mM NaCl, 2.68 mM KCl, 1.76 mM $KH_2PO_4$, 10.14 mM $Na_2HPO_4$). A volume ratio of 1:40 (liposome:buffer) is chosen to maintain a pseudo-sink condition for drug release. The dialysis bag is continuously agitated in an orbital shaker (Sartorius Cartomat, USA) maintained at 37° C. at 50 rpm. Aliquots are withdrawn from the release medium and is filtered through 0.2 µm syringe filter and collected in amber color HPLC sample bottle (2 ml, Agilent) followed by storage in the fridge at 4° C. until they are estimated. To obtain a closer approximation to the dynamic sink condition in the in-vitro setup, the dialysate is completely exchanged with fresh PBS buffer after every 24 hour and the released drug concentration in the dialysate is estimated accordingly, as previously discussed. Each experiment is repeated at least 3 times. The volume of liposomal formulation and the sizes of vesicle in the dialysis tube are recorded at the end of the release study to check any dilution effect of liposomal formulation and size changes of vesicles that occurred during drug release.

Drug Loading Efficiency

The observed encapsulation efficiency is in the range 75-88% for various formulations as reported in Table 1. The concentration of loaded drug after extrusion is estimated to be 200-660 µg/ml which is 4-12 fold higher than the Xalatan® (50 µg/ml) eye drop formulation whose normal dose requirement is one drop a day. The drug to lipid mole ratio (Table 2) after extrusion is higher than the initial value, which indicates that there is more partial loss (~20%) of lipid molecules than of drug molecules in the various stages of size reduction.

TABLE 2

Drug loading values before and after synthesis of liposome vesicles
Drug:Lipid mole ratio

| Initial | Final | Literature |
|---------|-------|------------|
| 0.030 | 0.044 ± 0.001 | 0.02 with ibuprofen in DPPC:Chol |
| 0.065 | 0.073 ± 0.002 | — |
| 0.086 | 0.104 ± 0.020 | — |
| 0.114 | 0.140 ± 0.020 | — |
| 0.143 | 0.180 ± 0.030 | — |
| 0.170 | 0.370 ± 0.050 | 0.29 with aryl-imidazole (ML220) in DSPC-PEG |

These mole ratios are much higher than the values obtained for a comparable lipophilic drug, ibuprofen, in the cholesterol-containing lipid vesicle of Mohammed et al., Liposome formulation of poorly water soluble drugs: optimization of drug loading and ESEM analysis of stability. Int J Pharm 285: pp. 23-34. The estimated mole ratios of drug/lipid are in the range between 0.04-0.37 (Table 2). The highest drug/lipid mole ratio obtained is nearly 3-5 times higher than earlier reported ibuprofen loading by Mohammed et al. However, this very high loading of latanoprost does not affect much on the vesicle stability (LUVs).

In Vitro Size Stability

The size measurements at various time intervals eg. W0 (initial), W2 (two weeks later), W4 (four weeks later) are carried out using the Zetasizer. From Table 3, it is seen that vesicles are reasonably stable while stored at 4° C. as long as the drug/lipid ratio is low.

Drug Release Behavior

Figure 8:
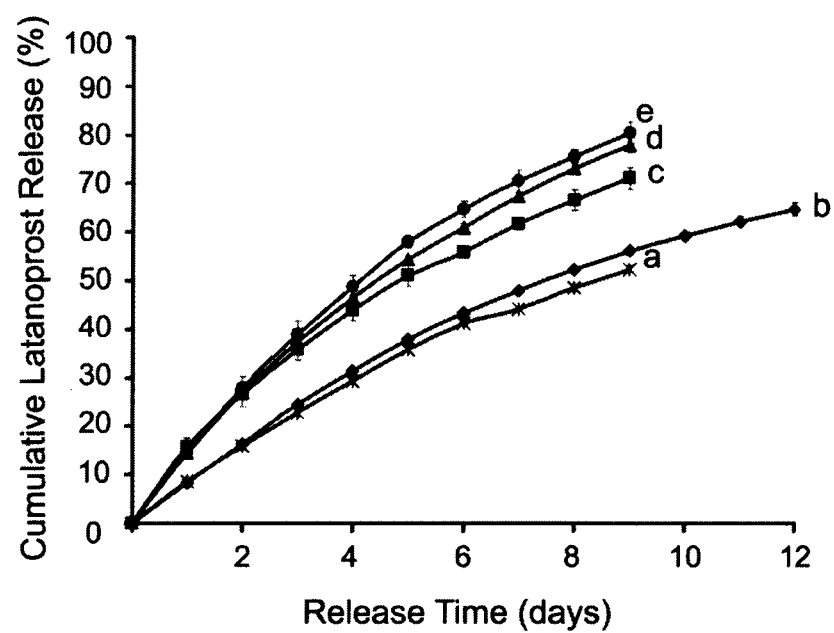
FIG. 8 shows a plot of in vitro dialysis study of latanoprost from drug loaded DPPC LUVs after extrusion, according to various embodiments.

Latanoprost release behavior from loaded liposomal formulations varying in d/l mole ratio, is expressed in terms of cumulative drug release (%) (FIG. 8). In FIG. 8, cumulative latanoprost release (%) from DPPC LUVs loaded with varying amount of drug/lipid mole ratios: (a) 0.044, (b) 0.11, (c) 0.14, (d) 0.18, (e) 0.37 is observed. Each value is the mean (standard deviations is plotted as error bars, which are always less than 3% for nearly all batches) of the results obtained from at least three independent experiments.

In order to better mimic the in vivo release condition, the buffer solution is exchanged every 24 hours with fresh PBS pH 7.4 maintained at 37° C. The release rate of any formulation increases with the initial drug concentration. There is no appreciable change between d/l mole ratio 0.04 to 0.11, but, beyond this limit the rate increases.

For a better understanding of the release pattern, vesicle sizes are recorded at the end of every release study (Table 3). For molar ratios lesser than d/l=0.14, the relative size variation is negligibly small; however, with higher amounts of drug, the size variations and polydispersity are higher, indicating probable vesicle destabilization during release, thus leading to faster drug release. The higher drug concentrations in the bilayer might affect the vesicle stability and thus accelerate drug release. Further understanding comes from estimation of thermal stability of drug loaded DPPC lipid bilayer using differential scanning calorimetry (DSC) measurements.

DSC Analysis

Figure 9:
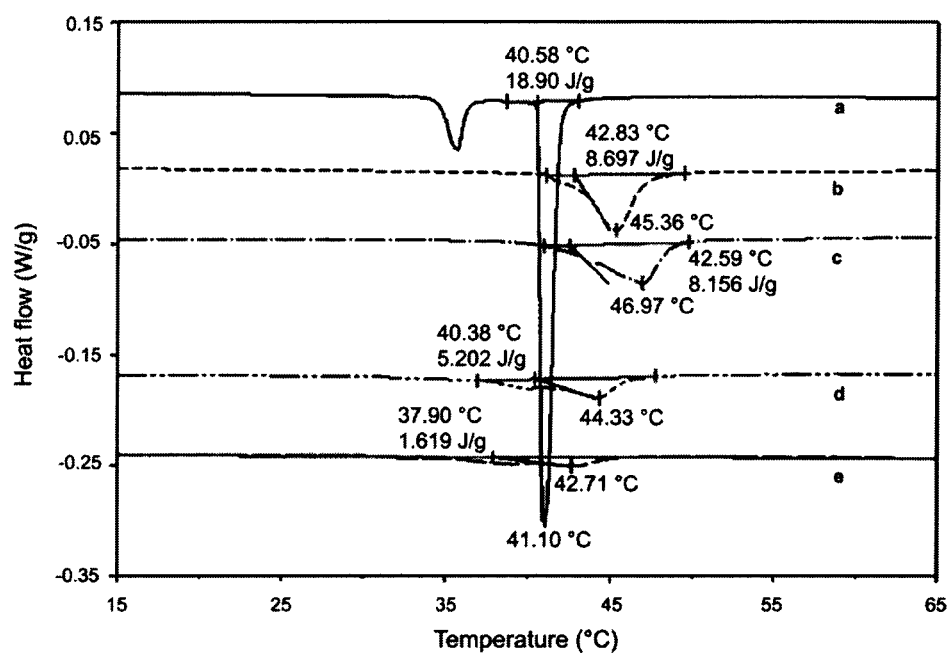
FIG. 9 shows DSC analysis of pure and latanoprost loaded DPPC MLVs, according to various embodiments.

FIG. 9 shows the DSC thermograms of different latanoprost loaded DPPC liposome. In FIG. 9, the liposome is made by PBS buffer hydration of anhydrous drug-lipid layer. 10 μl of the liposomal formulation (100 mg/ml) is heated at 1° C./min between −20° C. to 65° C. Three heating and two

TABLE 3

Size measurement of liposome formulation (varying d/l mole ratio) during storage at 4° C. and after in vitro drug release in PBS buffer (pH 7.4) at 37° C.

| Latanoprost/DPPC Liposome (actual) drug/lipid mole | Size measurement, nm (PDI) | | | | | After in vitro drug release |
|---|---|---|---|---|---|---|
| | W0 | W2 | W4 | W8 | W16 | |
| 0.00 | 82 (0.05) | 93 (0.06) | — | 91 (0.06) | 92 (0.06) | 93 (0.06) |
| 0.04 | 86 (0.05) | 89 | 102 (0.06) | 104 (0.06) | 104 (0.06) | 110 (0.06) |
| 0.07 | 111 (0.07) | 89 (0.06) | 98 (0.06) | 100 (0.06) | — | — |
| 0.10 | 109 (0.08) | 105 (0.10) | 105 (0.10) | — | 110 (0.10) | 150 (0.1) |
| 0.14 | 78 (0.06) | 93 (0.06) | 93 (0.08) | 101 (0.08) | 117 (0.10) | 145 (0.12) |
| 0.18 | 194 (0.10) | 210 (0.10) | 210 (0.10) | — | 310 (0.20) | 442 (0.20) |
| 0.37 | 118 (0.10) | 93 (0.10) | 93 (0.20) | 1015 (0.3) | 1176 (0.30) | 2020 (0.80) |

Effect of vesicle destabilization is noted when the d/l ratio exceeds 0.1. This is expected since the high loading would disrupt the structure of the bilayer, with shape distortion.

Figure 7:
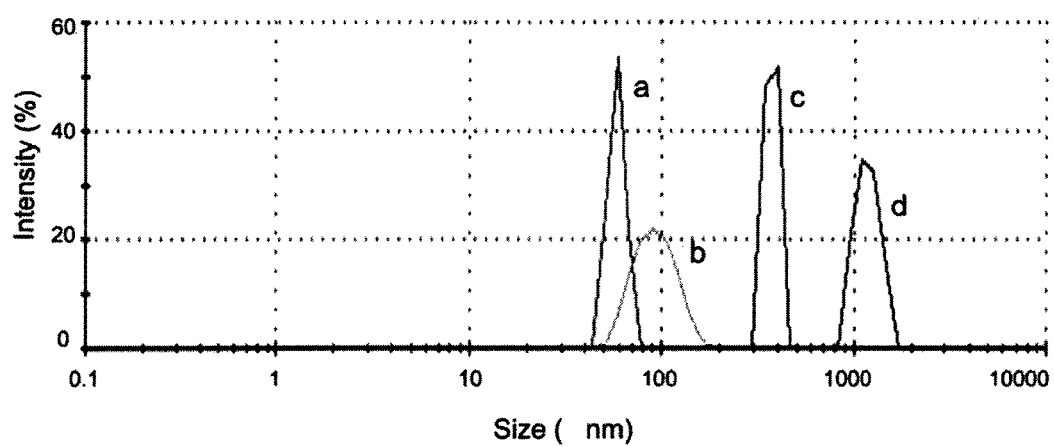
FIG. 7 shows a Malvern Zeta sizer analysis of drug loaded liposome, according to various embodiments.

FIG. 7 shows a Malvern Zeta sizer analysis which reflects the intensity (in %) corresponding to the sizes (or mean diameters) after 12 weeks of storage of drug-loaded vesicles at 4° C., and it is evident that the larger loading leads to greater size changes (all the vesicles start out at roughly the same size). In FIG. 7, the values are after 12 weeks of storage at 4° C. with d/l mole ratio (size, m): (a) 0.044 (63±10), (b) 0.11 (90±30), (c) 0.18 (200±80), (d) 0.37 (1250±200). Size measurement here are mean of three batches and the standard deviations (±) are expressed inside bracket.

cooling cycles are carried out with each sample and the last reproducible heating cycle is considered for analysis. The Drug/Lipid mole ratios and their corresponding enthalpy change during transition are reported within parentheses (a) 0.0 (18.9 J/g), (b) 0.03 (8.7 J/g), (c) 0.086 (8.1 J/g), (d) 0.114 (5.2 J/g), and (e) 0.14 (1.6 J/g).

The DSC shows endothermic transition for both drug-free and drug-loaded liposome. Plain DPPC liposome shows a sharp main transition (41.1° C.) with an expected pre transition at (35° C.) as well. As the drug/lipid mole ratio is increased, the pre transition disappears and the endothermic main transition broadens and shifts (FIG. 9). It is also interesting to note the shift is towards a higher temperature as the d/l mole ratio changes from 0 to 0.086 (41.1 to 47° C.). The trend then reverses and shifts towards lower temperature, although with a considerable peak broadening. With higher drug amount (d/l=0.114) the transition disappears completely. This observed effect could be an indication of the gradual change from more ordered liquid to more disordered liquid behavior, caused by excessive drug incorporation. The peak broadening with latanoprost incorporation resembles the trend reported for cholesterol in DPPC lipid bilayer.

The lipophilic latanoprost molecules would preferentially locate themselves in the lipid bilayer, and thus might influence the stability of the bilayer. Excess drug loading may affect stability of vesicles, which could yield a "leakier" liposome and thus faster release.

Partition Coefficient of Latanoprost in DPPC Liposome

Figure 10:
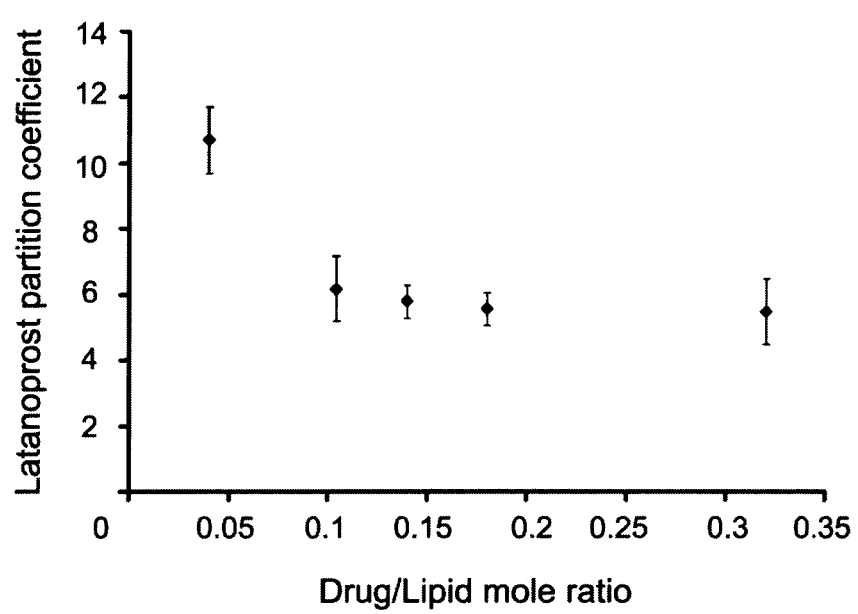
FIG. 10 shows a plot of partition coefficient of latanoprost, according to various embodiments.

The ratio of drug concentration in the lipid bilayer to that in the continuous phase is defined as partition coefficient (P.C.), as discussed earlier. As shown in FIG. 10, a decrease in partition coefficient from 11.0±1 to 6.0±1 is observed upon varying the d/l mole ratios from 0.04 to 0.104. However, with any further increase in the d/l mole ratios up to 0.32, no differences in the partition coefficient are observed. In FIG. 10, partition coefficient of latanoprost is calculated by taking the ratio of drug concentrations in lipid bilayer and the aqueous buffer. The drugs to lipid loading concentrations (mole ratios) are 0.04, 0.104, 0.14, 0.18, and 0.32 in DPPC. Each partition coefficient value is obtained from the mean of three MLV formulations made and the standard deviations are reported in error bars.

Selection of DPPC Liposome Formulation for In Vivo Studies in Rabbit Eyes

The data is based on the vesicle storage stability, DSC analysis, drug partition coefficient and daily dose requirement. A liposomal formulation of d/l mole ratio of 0.104 is chosen to study the IOP lowering effect in the rabbit eye, since the current eye drop administration of Xalatan® amounts approximately to 1.5 µg/drop/day.

Figure 11:
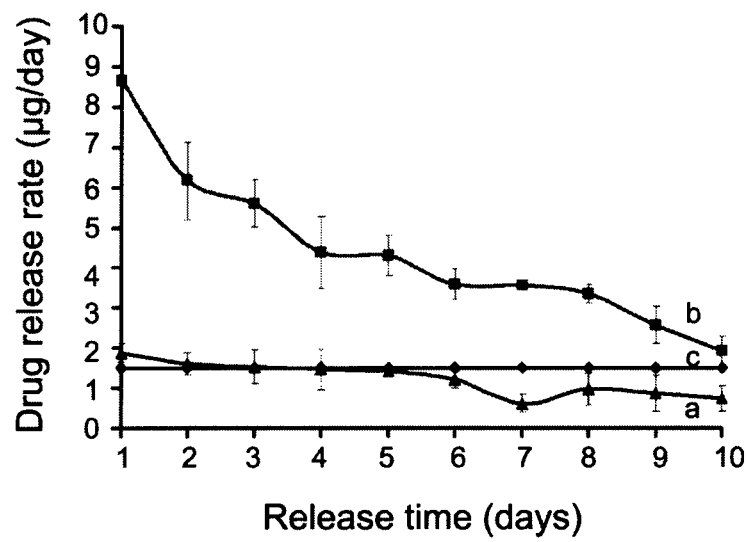
FIG. 11 shows a plot of Latanoprost release rate, according to various embodiments.

In the sub-conjunctival administration of the liposomal latanoprost, it is intended to target a similar dose/day sustained for at least 10 days, assuming a subconjunctival injection volume of 100 µL. The in vitro release rate (per day) is plotted for two candidate formulations of DPPC-latanoprost, at d/l ratios of 0.04 and 0.104, in FIG. 11 shown for comparison with the daily dose of Xalatan® eye drop. FIG. 11 shows a Latanoprost release rate from 100 µl of DPPC LUVs with two different d/l mole ratios compared with 1 drop of commercial Xalatan® solution (1.5 µg/drop). In FIG. 11, in vitro drug release rate (µg/day) measured from: (a) d/l, 0.04 and (b) 0.11, (c) commercial eye drop (Xalatan®, 1.5 µg/drop). The release rates are reported based on mean values of at least two batches and standard deviations are reported in error bars.

Although the d/l mole ratio of 0.04 matches the eye drop, its daily rate dips below Xalatan beyond Day 5, and hence, is unsuitable for sustained delivery. Thus, it is opted to use the DPPC-latanoprost formulation at a d/l mole ratio of 0.104 for the rabbit study, even though it demonstrated a higher initial burst release in vitro.

Topically Applied Liposomal Formulation

Topical administration for the DPPC-latanoprost formulation, mimicking the eye drop administration of Xalatan® is considered. However, IOP measurement in all the rabbits does not show any IOP reduction (data not reported) compared to the Xalatan® eye drop. This shows that latanoprost loaded neutral DPPC liposomal formulation once applied topically cannot enter through corneal epithelium. This mode of administration of the liposomal formulation is not considered further and only the sub-conjunctival injection is compared to the eye drop in the rabbit studies.

Figure 12:
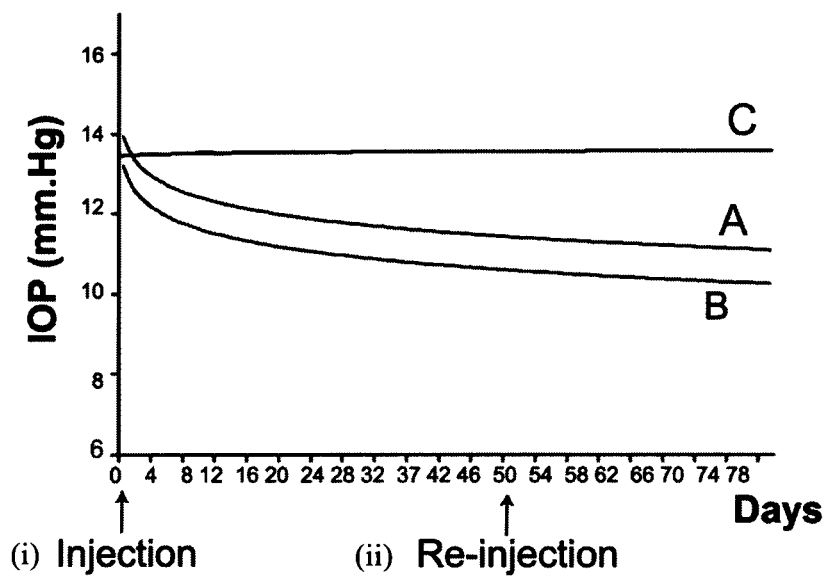
FIG. 12 shows a plot of comparison of intraocular pressure (IOP) between topical latanoprost eyedrop, subconjunctival latanoprost liposome and latanoprost-free blank liposomes: Group A: topical latanoprost eye drop. Group B: subconjunctival latanoprost liposome. Group C: latanoprost-free blank liposomes.

Effects of Intraocular Pressure from Subconjunctival Injection of Latanoprost/Liposomal Formulation The baseline IOP is 13.6±0.3 mmHg for all 23 rabbits and there is no significant difference between all 3 groups (P=0.81) evaluated. A significantly higher mean reduction of IOP in the subconjunctival latanoprost-loaded liposome (group B) compared to topical latanoprost eye drop (group A) is observed. At 30 days IOP reduces by 3.0±0.17 mmHg in group B versus 1.6±0.18 mmHg in group A (P<0.001) and at 80 days the IOP reduces by 3.5±0.60 vs. 2.3±0.61 mmHg respectively (P<0.001) as shown in FIG. 12. In FIG. 12, points (i) and (ii) refers to a point of injection and a point of re-injection, respectively.

Subconjunctival Injection of Latanoprost/Liposome Formulation

Figure 13A:
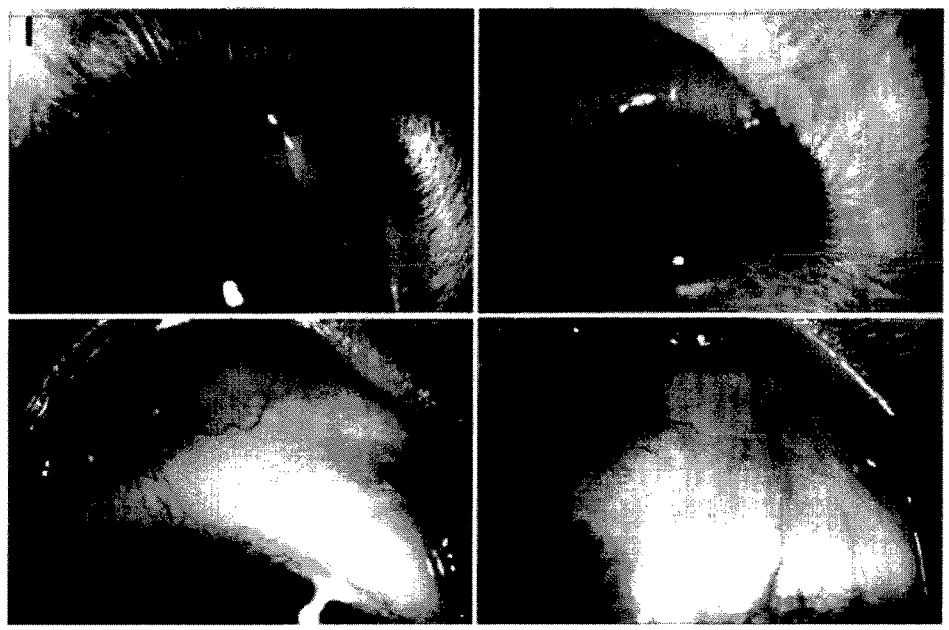
FIG. 13 shows (A) photo images and (B) ASOCT scans of a rabbit eyes condition after subconjunctival injection.
Figure 13B:
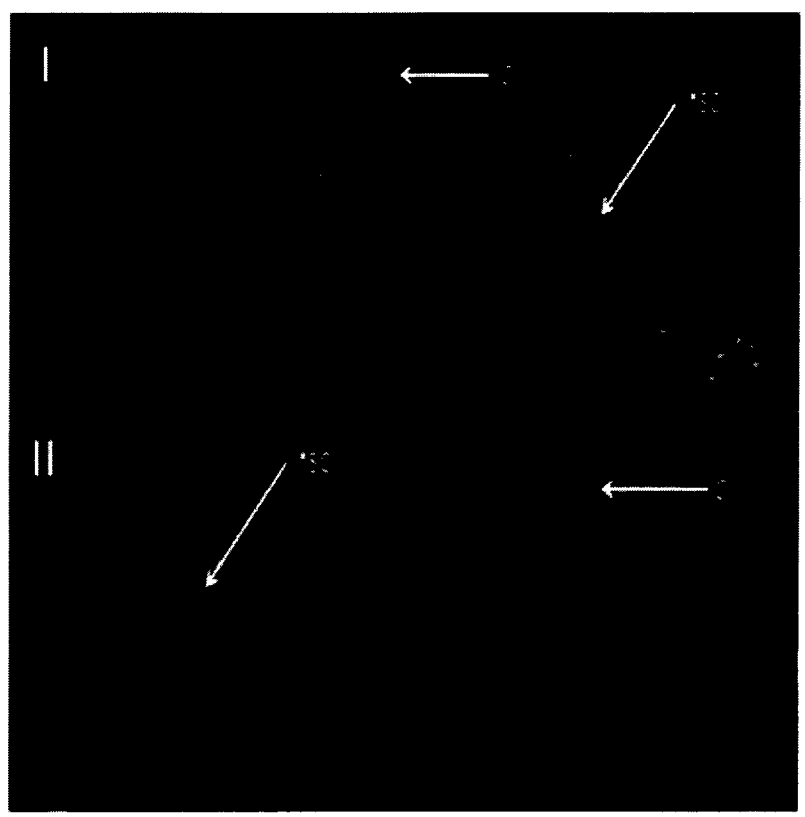

The clinical effect of injecting the liposome formulation on conjunctival vascularity shortly after administering the subconjunctival injection is recorded and at Day 30 in each treatment group. No significant increase in conjunctival vascularity in any of the eyes from the 3 groups is noted. Furthermore, no complications such as conjunctival infection, ulceration or anterior chamber inflammation on slit-lamp examination have been observed (FIG. 13A, I and II: Day 0 after subconjunctival injection; III and IV: Day 30 after subconjunctival injection). The surrounding conjunctiva is white and the eyelids do not show any signs of swelling or inflammation. Finally, ASOCT scans confirm the subconjunctival placement of the injected liposomes in the superior temporal aspect of each rabbit eye (Photos I and II in FIG. 13B, *SC=Liposome injection site; C=Cornea.). Subsequent ASOCT scans do not reveal any abnormal conjunctival scarring or scleral thickening at the injection sites, thus supporting the slit lamp observations.

Histology

Figure 14A:
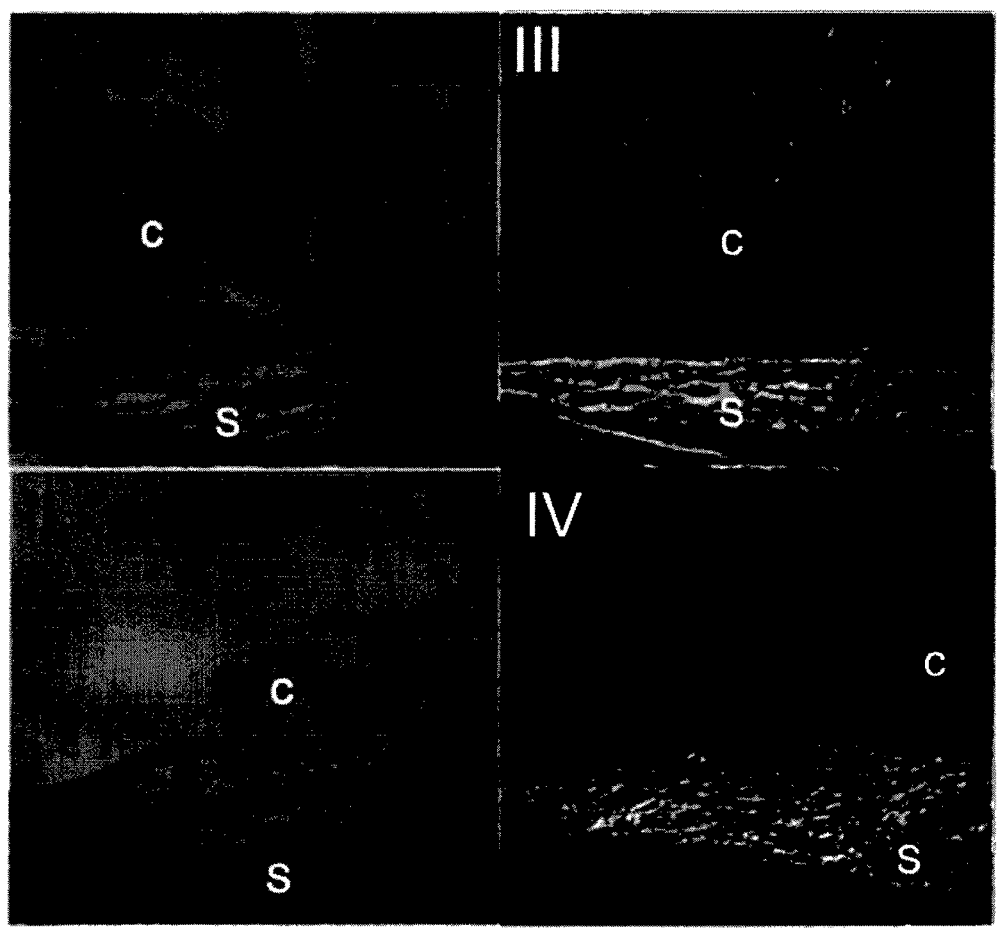
FIG. 14 shows histology of rabbit eyes—A: topical latanoprost eyedrops, B: subconjunctival latanoprost liposomes, and C: subconjunctival latanoprost-free liposomes.
Figure 14B:
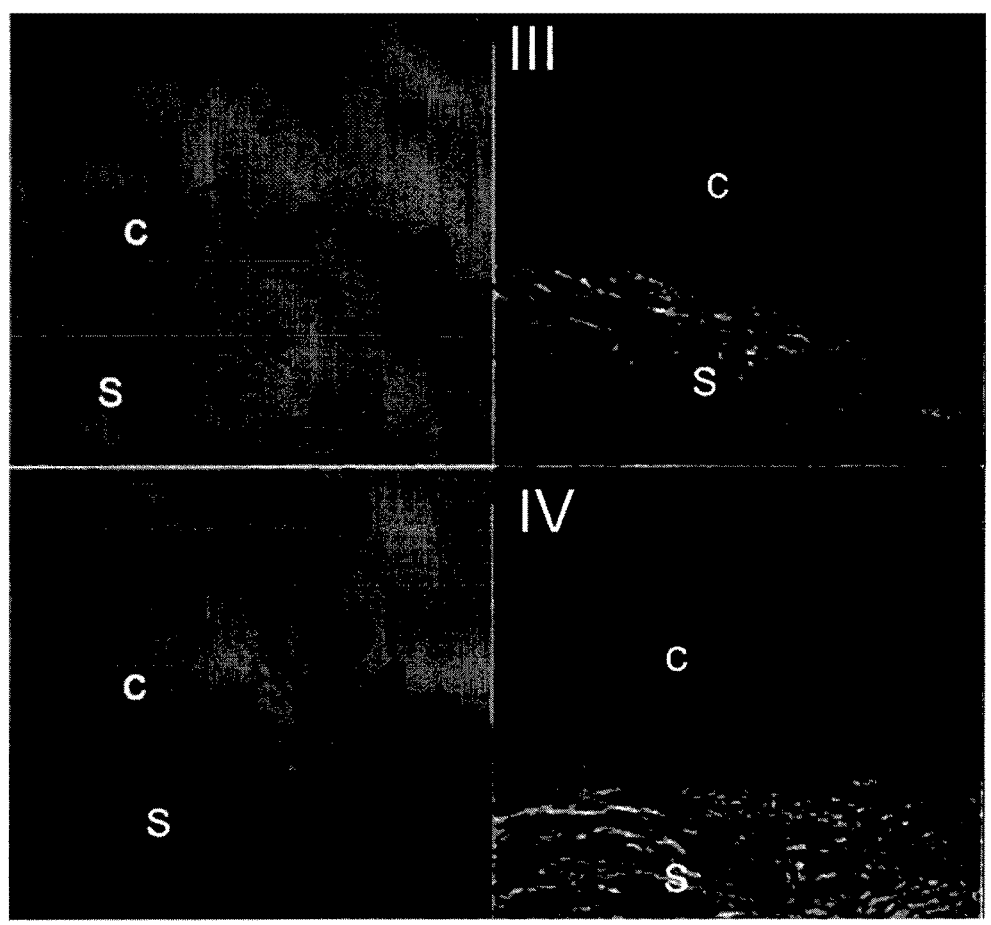
Figure 14C:
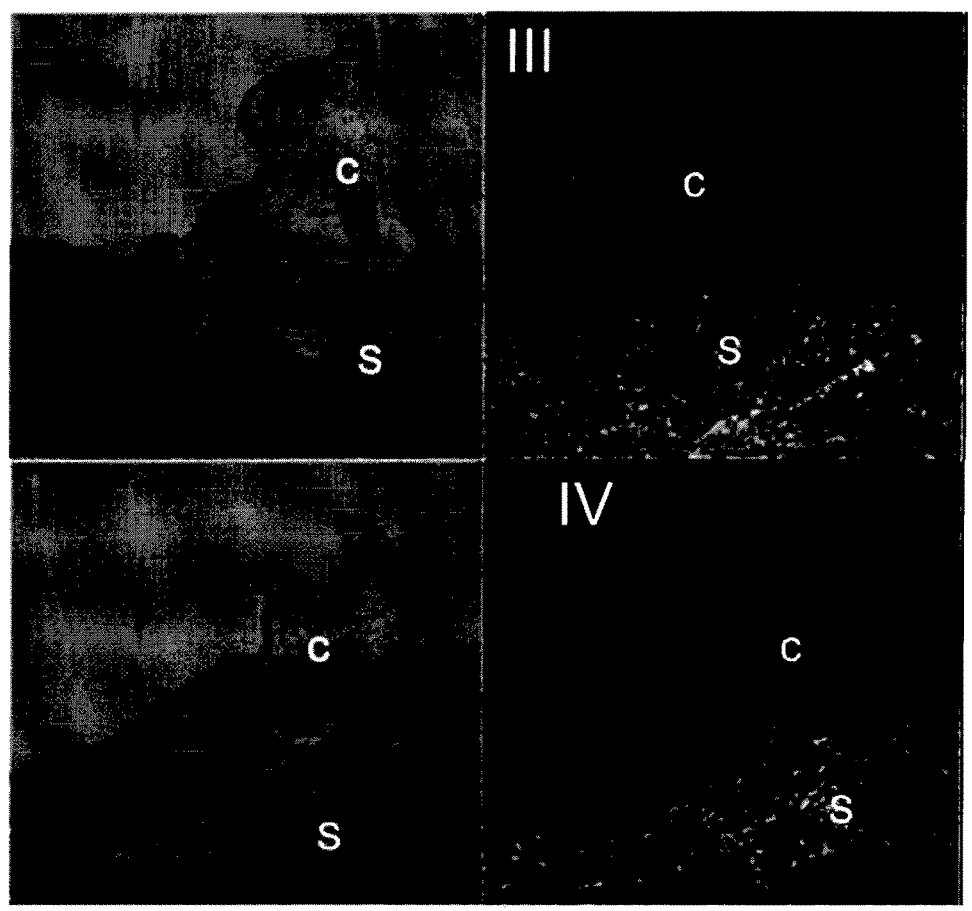

The surrounding conjunctival tissue does not reveal any significant inflammation or fibrosis on histological examination of all the enucleated eyes. Sirius red polarizing microscopy of collagen fibers also reveals no significant increase in the amount of fibrosis in all 3 groups (FIG. 14). In FIG. 14, Group A: topical latanoprost eyedrops. Group B: subconjunctival latanoprost liposomes. Group C: subconjunctival latanoprost-free liposomes. Histology reveals no abnormal scarring or damage to the collagen layers in both H&E stain (Photos I and II) and Picrosirius red stain (Photos III and IV; Grade 1 for all eyes). S=Sclera; C=Conjunctiva.

It is now recognized that there is a medical need for sustained delivery of eye drops needed for chronic diseases such as glaucoma. One such agent, a prostaglandin derivative, latanoprost for incorporation into liposomes for sustained delivery are selected. High (75-88%) drug loading into the DPPC liposomes are obtained. The lipophilic nature of latanoprost with a log P=4.4 (Data from SRC PhysProp Database) clearly indicates that the loaded drug resides predominantly in the bilayer. However, a measurable amount of latanoprost also resides in the aqueous phase outside of the liposomes. This is reflected in the measured partition coefficients, which vary from about 12 to 6, depending on initial drug loading. These numbers translate to about 8% and 17% "free drug" outside of the liposomes. Free drug removal from the formulation is not carried out, as removal requires a fairly lengthy process. Removal of free lipophilic drug (ibuprofen) from liposomal formulation is also not routinely performed. Therefore, all the experiments and analyses are based on the formulation obtained after extrusion step, which contains mostly liposome-incorporated latanoprost, with about 17% free drug in the case of the 0.104 d/l mole ratio formulation.

The drug/lipid mole ratio estimated here is nearly 3-5 times more than earlier reported lipophilic drugs eg. Ibuprofen and Cisplatin. A similar higher loading of lipophilic anti-cancer drug aryl-imidazole compound (ML220) loaded in DSPE-PEG liposome have a 3 weeks of stability at the incubation temperature (37° C.).

Storage stability analysis shows that vesicles with no drug or with lower drug amounts (d/l 0.14) remain unaffected. When the quantity of drug is increased to d/l 0.18 and above, destabilization is noted from 4 weeks onwards. Size analysis after drug release at 37° C. in PBS buffer shows similar behavior to that during storage. The destabilization is magnified at the higher d/l mole formulations. A possible explanation for the destabilization of the vesicles with increase in loading lies in the interactions of latanoprost with the bilayer acyl/phosphate head group of DPPC liposomes. Latanoprost molecules (at high loading) could possibly weaken the hydrogen bonding between the phosphate head groups that hold vesicle together. However; this postulate remains to be confirmed with suitable studies. Thus, vesicles with a lesser amount of drug (till d/l mole 0.14) are stable for at least one month.

In general, it is noted drug release rate to increase with an increase in d/l mole ratios. There are currently no accepted models for the release of drugs from liposomes. If the liposomal carriers are treated as "monolithic matrices" and assume mainly diffusional release of drug, then for either dissolved or dispersed drug, a decrease in rate with loading rather than an increase is expected. However, no dependence on loading when the d/l ratios ranged from 0.04 to 0.11 is observed, but an increase in rate with loading for d/l>0.11 is seen. This increase is attributable to a more "destabilized" vesicle in terms of size increase during the release study (Table 3), which implies the creation of a larger vesicle bilayer more permeable to diffusion. Beyond d/l ratios of 0.11, the latanoprost appears to be loaded beyond its saturation limit in the bilayer, and as a consequence, the metastable bilayer changes in size over time from being destabilized.

The thermal stability (DSC) analysis of drug loaded DPPC liposome indicates peak broadening with drug loading. The sharp transitions (pre- and main) disappear (FIG. 9) with drug incorporation. Peak broadening due to incorporation of cholesterol in DPPC bilayer is observed and this is attributed to probable loss of crystalline nature of DPPC lipids. However, unlike cholesterol incorporation into DPPC, which leads to a drop in transition temperature, latanoprost loaded DPPC liposomes behave differently. At the release condition, the bilayer is expected to remain in the rigid gel phase (high crystalline) for DPPC (Tc=41.1° C.). With lower amount of drug/lipid mol ratio there is an increase in transition temperature from 41.1° C. for d/l=0 to 44.8° C. for d/l=0.04 and 46.6° C. with d/l=0.086. A similar peak broadening and rise in transition temperature with higher incorporation of cholesterol in DPPC liposome has been previously observed. At high molar concentrations, cholesterol exists as a sterol rich domain (also called "non-cooperative zone") leading to peak broadening and a shift towards higher temperature. This domain formation is also reflected in an increase in vesicle diameter which is similar to our observation with higher mole % of latanoprost in DPPC (Table 3). DPPC lipid volume is estimated to be ~1200 Å3/molecule (of which ~900 Å3 is for acyl chains and rest ~300 Å3 for phosphate head group) while the latanoprost molecule has an approximate volume of ~500 Å3 based on molecular dynamic calculations. With increased proportion of latanoprost, gradually the lipid-latanoprost interaction increases due to bilayer space constraint, which may lead to an increase in transition temperature of the binary system. However, the existence of a maximum in the transition temperature (with d/l ratio) requires further investigation. The enthalpy change (FIG. 9) at the main transition with pure DPPC (18.9 J/g) gradually decreases to 8.7, 8.1, 5.2, 1.6 J/g respectively with increase in drug/lipid mole ratios at 0.03 (b), 0.086 (c), 0.114 (d), 0.14 (e). This also supports the postulated latanoprost-lipid interaction that renders the bilayer more fluidic or disordered.

Partition coefficient analysis indicates a drop in drug distribution between the lipid bilayer and the continuous phase, with increased drug loading. After the initial decrease (from about 11 to about 6), the partition coefficient remains unaltered. The partition coefficient gives an estimate of the drug distribution between the lipid bilayer and the continuous phase. The method of lipophilic drug incorporation also strongly influences the partition coefficient value.

For smaller drug quantities such as d/l=0.04 mole, the drug molecules prefer to remain in the bilayer as entrapped drug and the rest as free drug in the buffer. The accumulation of the drug in the bilayer is limited by the bilayer area available in the vesicles. Favorable drug-bilayer interactions could increase this bilayer loading as well. For higher drug loading amounts, there is a significant amount of the drug existing as free drug in the continuous buffer phase of the liposomes, as the bilayer gets saturated with drug molecules. This appears to explain the decrease seen in the partition coefficient values seen in our study In vivo studies reveal that a single depot subconjunctival injection of latanoprost-loaded liposome results in a sustained, therapeutic lowering of IOP beyond 50 days. The extent of IOP lowering is significantly better using the liposomal formulation than free latanoprost administered daily via eye drop, the current 'standard of treatment' in glaucoma patients. This is consistent with in vitro data that shows a sustained release (and a higher amount released compared to the eye drop) over 10 days, while maintaining vesicle size and shape. The significant and sustained reduction of IOP in rabbit eyes is encouraging, and there appears to be no other reports that show such a dramatic improvement in latanoprost sustainability by DPPC liposomes via subconjunctival injections in an animal eye. Slit-lamp microscopy, histology and imaging techniques such as AS-OCT are used to demonstrate that these liposomes appear to be well tolerated in an animal eye, biocompatible and do not cause any obvious clinical adverse effects to the ocular tissues with the subconjunctival injection of the liposomal carrier.

Because of the measured higher initial rate of drug release from the DPPC formulation, there have been concerns about side effects during initial stages following injection. However, throughout the duration of the study, no obvious effect has been detected with the methods used for clinical monitoring. There is also no residual drug either in the aqueous or vitreous humor at the end of study. It is also interesting to note that repeat injections of drug loaded DPPC liposome treatment does not result in any hyperpigmentation to the cornea or conjunctiva. Unlike the commercial eye drop (Xalatan®), the present formulation is devoid of any preservatives such as benzalkonium chloride (BAK), which is thought to be the root cause of the cornea pigmentation. The short period of exposure to the drug may also be a reason for the absence of clinical corneal changes.

Example 4

Determining the Effect of Stearyl Amine on DPPC Liposome

Example 4

Materials

Ocular Drug: Latanoprost
Phospholipids: DPPC (Sample 15-a), DPPC with stearyl amine of an amount of 10% by weight (Sample 15-b), DPPC with stearyl amine of an amount of 20% by weight (Sample 15-c)
Liposomal formulation of ocular drug having a drug-to-liposome mole ratio of 0.035.
Procedure
As per in Example 3.

Figure 15:
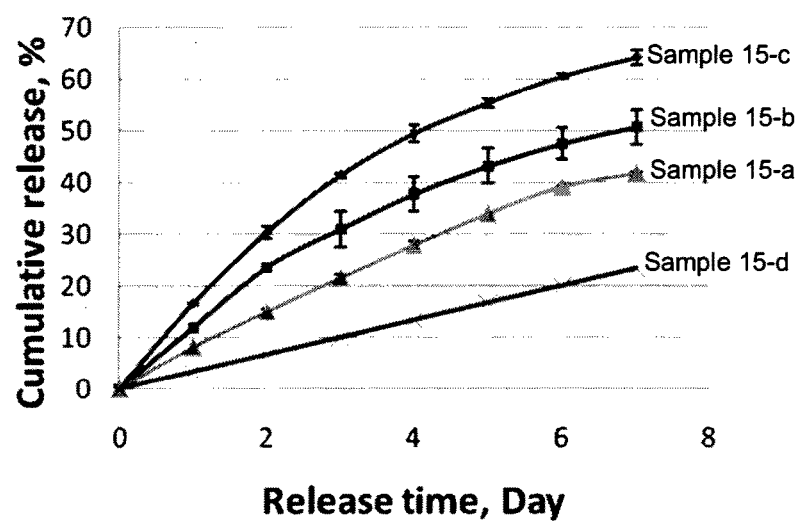
FIG. 15 shows a plot of drug-release curves for liposomal formulations involving DPPC according to various embodiments.

FIG. 15 shows the release curves of latanoprost from DPPC LUVs with and without added stearyl amine. The vertical Y-axis of the plot in FIG. 15 labeled as "cumulative release, %" refers to the percentage of the amount of drug being released from liposomal formulation over the total amount of drug contained in the liposomal formulation. The horizontal X-axis of the plot in FIG. 15 labeled as "release time, day" refers to the n-th day of monitoring the drug release where n is 0, 1, 2, 3, 4, 5, 6, 7, . . . A desired rate for latanoprost release (Sample 15-d) is also included in FIG. 15 for comparison purposes. Similar to Example 2, this desired rate reflects the rate at which latanoprost is released based on an eye drop formulation. In FIG. 15, the error bars shown refer to standard deviations.

In FIG. 15, it is shown that the addition of stearyl amine to DPPC gives average release rates higher than the desired release rate for latanoprost based on an eye drop formulation. It is also shown that higher daily release rates of about 6% to 15% are observed for the liposomal formulations as compared to that of the eye drop formulation, which has a daily release rate of about 4% for the period between the $0^{th}$ and $4^{th}$ day of release, while similar daily release rates of about 4.25%±0.75% are observed for the respective liposomal formulations and the eye drop formulation for the period between the $5^{th}$ and $7^{th}$ day of release.

From FIG. 15, it can be concluded that the addition of stearyl amine to DPPC helps to retain the liposomes in the front of the eye for longer periods. In Example 4, all samples of different liposomal formulation (i.e., Samples 15-a to 15-c) are optically clear. Similar observations on the trends of average release rates and daily release rates without substantially lowering the release rate are made for liposomal formulations for ocular drug delivery having a drug-to-lipid mole ratio of up to 0.5, and having stearyl amine in an amount of about 10% to about 20% by weight of the liposomes.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The Invention claimed is:

1. A liposomal formulation for ocular drug delivery comprising:
   (i) liposomes comprising at least one lipid bilayer; and
   (ii) latanoprost encapsulated in the liposomes,
wherein the liposomes have a mean diameter of 100 nm to 300 nm, the liposomes comprise phosphatidylcholine, the liposomal formulation is a sustained release formulation having a latanoprost to lipid mole ratio of 0.01:1 to 0.50:1, less than 60% of the latanoprost encapsulated in the liposomes is released from the liposomes in 10 days, as measured by an in vitro release assay, and egg phosphatidylcholine is the only phosphatidylcholine in the liposomal formulation.

2. The liposomal formulation as claimed in claim 1, wherein the liposomal formulation has a latanoprost to lipid mole ratio of 0.01:1 to 0.37:1.

3. The liposomal formulation as claimed in claim 2, wherein the liposomal formulation has a latanoprost to lipid mole ratio of 0.015:1 to 0.37:1.

4. The liposomal formulation as claimed in claim 3, wherein the liposomal formulation has a latanoprost to lipid mole ratio of 0.04:1 to 0.37:1.

5. The liposomal formulation as claimed in claim 1, wherein the liposomes further comprise at least one sphingolipid, sterol lipid, saccharolipid, or polyketide lipid.

6. The liposomal formulation as claimed in claim 5, wherein the sphingolipid comprises at least one unsaturated fatty acid moiety.

7. The liposomal formulation as claimed in claim 6, wherein the sphingolipid comprises hexadecanoylsphingomyelin or egg sphingomyelin.

8. The liposomal formulation as claimed in claim 1, wherein the liposomal formulation has a latanoprost to lipid mole ratio of 0.50:1.

9. The liposomal formulation as claimed in claim 1, wherein the liposomal formulation has a latanoprost to lipid mole ratio of 0.18:1.

10. The liposomal formulation as claimed in claim 1, wherein the liposomal formulation has a polydispersity index of less than or equal to 0.25.

11. The liposomal formulation as claimed in claim 1, wherein the liposomes further comprise cholesterol.

12. The liposomal formulation as claimed in claim 11, wherein the cholesterol is of an amount of about 10% to about 40% by weight of the liposomes.

13. The liposomal formulation as claimed in claim 1, wherein the liposomes further comprise a linear $C_8$-$C_{20}$ alkyl or alkenyl amine.

14. The liposomal formulation as claimed in claim 13, wherein the linear $C_8$-$C_{20}$ alkyl or alkenyl amine is stearyl amine.

15. The liposomal formulation as claimed in claim 14, wherein the stearyl amine is present at 5% to 25% by weight of the liposomes.

16. The liposomal formulation as claimed in claim 15, wherein the stearyl amine is present at 10% to 20% by weight of the liposomes.

17. A pharmaceutical composition comprising a sustained release liposomal formulation comprising:
   (i) liposomes comprising at least one lipid bilayer; and
   (ii) latanoprost encapsulated in the liposomes,
wherein the liposomes have a mean diameter of 100 nm to 300 nm, the liposomes comprise phosphatidylcholine, the liposomal formulation has a latanoprost to lipid mole ratio of 0.01:1 to 0.50:1, less than 60% of the latanoprost encapsulated in the liposomes is released from the liposomes in 10 days, as measured by an in vitro release assay, and egg phosphatidylcholine is the only phosphatidylcholine in the liposomal formulation.

18. The pharmaceutical composition as claimed in claim 17, wherein the liposomal formulation has a latanoprost to lipid mole ratio of 0.01:1 to 0.37:1.

19. The pharmaceutical composition as claimed in claim 17, wherein the liposomal formulation has a latanoprost to lipid mole ratio of 0.015:1 to 0.37:1.

20. The pharmaceutical composition as claimed in claim 19, wherein the liposomal formulation has a latanoprost to lipid mole ratio of 0.04:1 to 0.37:1.

21. The pharmaceutical composition as claimed in claim 17, wherein the pharmaceutical composition is in the form of an ophthalmic solution.

22. The pharmaceutical composition as claimed in claim 17, wherein the pharmaceutical composition is formulated for ocular drug delivery as an injection solution or a viscous aqueous vehicle.

23. The pharmaceutical composition as claimed in claim 17, wherein the pharmaceutical composition is formulated for ocular drug delivery as a viscous aqueous vehicle, wherein the viscous aqueous vehicle comprises an aqueous solution of a polysaccharide.

24. The pharmaceutical composition as claimed in claim 23, wherein the polysaccharide is hyaluronic acid.

25. A method for treating an ocular disease, comprising administering a sustained release liposomal formulation to the eye of a subject in need thereof, the liposomal formulation comprising:

(i) liposomes comprising at least one lipid bilayer; and
(ii) latanoprost encapsulated in the liposomes, wherein the ocular disease is glaucoma, the liposomes have a mean diameter of 100 nm to 300 nm, the liposomes comprise phosphatidylcholine, the liposomal formulation has a latanoprost to lipid mole ratio of 0.01:1 to 0.50:1, less than 60% of the latanoprost encapsulated in the liposomes is released from the liposomes in 10 days, as measured by an in vitro release assay, and egg phosphatidylcholine is the only phosphatidylcholine in the liposomal formulation.

26. The method as claimed in claim 25, wherein the liposomal formulation is administered by subconjunctival injection.

* * * * *